United States Patent [19]
Peshwa et al.

[11] Patent Number: 6,121,044
[45] Date of Patent: *Sep. 19, 2000

[54] POTENT ANTIGEN PRESENTING CELL COMPOSITION

[75] Inventors: Madhusudan Viswanath Peshwa; Willem Caspar Anton van Schooten, both of Sunnyvale, Calif.

[73] Assignee: Dendreon Corporation, Seattle, Wash.

[ * ] Notice: This patent issued on a continued prosecution application filed under 37 CFR 1.53(d), and is subject to the twenty year patent term provisions of 35 U.S.C. 154(a)(2).

[21] Appl. No.: 08/501,987

[22] Filed: Jul. 12, 1995

[51] Int. Cl.[7] .............................. C12N 5/00; C12N 5/02; C12N 5/06

[52] U.S. Cl. ..................... 435/325; 435/372; 435/373; 435/375; 435/395; 435/382; 435/2

[58] Field of Search ..................... 435/325, 372, 435/373, 382, 375, 395, 2; 424/184.1, 529

[56] References Cited

FOREIGN PATENT DOCUMENTS

WO 93/20185  10/1993  WIPO.
WO 93/20186  10/1993  WIPO.
WO 94/02156   2/1994  WIPO.

OTHER PUBLICATIONS

O'Doherty, U., et al., "Dendritic Cells Freshly Isolated from Human Blood Express CD4 and mature into Typical Immunostimulatory Dendritic Cells after Culture in Monocyte–Conditioned Medium," *J. Exp. Med.* 178:1067–1078 (1993).

Peters, J.H., et al., "Signals Required for Differentiating Dendritic Cells from Human Monocytes In Vitro," in *Dendritic Cells in Fundamental and Clinical Immunology* (Kamperdijk, et al., Eds.) Plenum Press, New York, NY, pp. 275–280 (1993).

Takahashi, H., et al., "Induction of $CD8^{#}$ Cytotoxic T Lymphotcytes by Immunization with Syngeneic Irradiated HIV–1 Envelope Derived Peptide–Pulsed Dendritic Cells," *Int. Immunol.* 5(8):849–857 (1993).

Thomas, R., and Lipsky, P.E., "Human Peripheral Blood Dendritic Cell Subsets: Isolation and Characterization of Precursor and Mature Antigen–Presenting Cells," *J. Immunol.* 153:4016 (1994).

Zhou, L.J., and Tedder, T.F., "Human Blood Dendritic Cells Selectively Express CD83, A Member of the Immunoglobulin Superfamily," *J. Immunol.* 154:3821–3835 (1995).

Austyn, J.M., et al., "Isolation and Characterization of Dendritic Cells from Mouse Heart and Kidney," *Immunology* 152:2401–2410 (1994).

Giessler, R.K.H., et al., "Dendritic Accessory Cells Derived from Rat Bone Marrow Precursors Under Chemically Defined Conditions In Vitro Belong to the Myeloid Lineage," *Eur. J. Cell Biol.* 45:171–181 (1991).

Giessler, R.K.H., et al., "Serum–Free Differentiation of Rat and Human Dendritic Cells, Accompanied by Acquisition of the Nuclear Lamins A/C as Differentiation Markers," *Dendritic Cells in Fundamental and Clinical Immunology* (Kamperdijk, et al., Eds.) Plenum Press, New York, NY, pp. 287–291 (1993).

Kabal, P.J., et al., "Accessory Cells with a Morphology and Marker Pattern of Dendritic Cells Can Be Obtained from Elutriator–Purified Blood Monocyte Fractions –An Enhancing Effect of Metrazamide in this Differentiation," *Immunobiol.* 179:395–411 (1989).

Mehta–Damani, A., et al., "Generation of Antigen–Specific $CD8^{#}$ CTLs from Naive Precursors," *J. Immunol.* 153:996 (1994).

Najar, H.M., et al., "Differentiation of Human Monocytes into Accessory Cells at Serum–Free Conditions," *Eur. J. Cell Biol.* 51:339–346 (1990).

Mahnke, K., et al., "Upregulation of Dendritic Cell Allostimulatory Capacity, Cytokine Production and Expression of Heat–Stable Antigen by Incubation on Collagen–Coated Plates," *J. Invest. Dermatol.* 104(4):565 Abstract (1995).

Markowitcz, S., and Engleman, E.G., "Granulocyte–Macrophage Colony–Stimulating Factor Promotes Differentiation and Survival of Human Peripheral Blood Dendritic Cells In Vitro," *J. Clin. Invest.* 85(3):955 (1990).

Ried, C.D.L., et al., "Interactions of Tumor Necrosis Factor with Granulocyte–Macrophage Colony–Stimulating Factor and Other Cytokines in the Regulation of Dendritic Cell Growth In Vitro from Early Bipotent $CD34^{#}$ Progenitors in Human Bone Marrow," *J. Immunol.* 149(8):2681–2688 (1992).

Uren, S., et al., "Factors Affecting the Generation of Dendritic Cells by Culture of Human Monocytes in Serum–Free Medium," *Trans. Proceed.* 25(5):2910–2912 (1993).

Beaulieu, S., "An Improved Method for Purifying Human Thymic Dendritic Cell," *J. Immunol. Methods* 180(2):225–236 (1995).

Grabbe, S., et al., "Dendritic Cells as Initiatiors of Tumor Immune Responses: a Possible Strategy for Tumor Immunotherapy?" *Immunol. Today* 16(3):117 (1995).

Lu, L., et al., "Propagation of Dendritic Cell Progenitors from Normal Mouse Liver Using Granulocyte/Macrophage Colony–Stimulating Factor and Their Maturational Development in the Presence of Type–1 Collagen," *J. Exp. Med.* 179:1823–1834 (1994).

(List continued on next page.)

*Primary Examiner*—David Saunders
*Assistant Examiner*—F. Pierre VanderVegt
*Attorney, Agent, or Firm*—Dehlinger and Associates; Linda R. Judge

[57] ABSTRACT

A method of obtaining a blood-cell fraction enriched for potent antigen presenting cells is disclosed. The method includes obtaining a monocyte-depleted lymphocyte fraction, culturing the cell fraction in a serum-free medium for a period sufficient to produce a morphological change in dendritic-precursor cells to cells having the morphology of dendritic cells, harvesting non-adherent cells produced by said culturing, and enriching the portion of dendritic cells in the harvested cells by density centrifugation. Also disclosed is a PAP cell composition containing cells enriched for PAP activity in a collagen matrix.

7 Claims, 12 Drawing Sheets

OTHER PUBLICATIONS

Metrakos, P., et al., "Collagen Gel Matrix Promotes Islet Cell Proliferation," *Transplant. Proceed.* 26(6):3349–3350 (1994).

Brendel, M.D., et al., "Improved Functional Survival of Human Islets of Langerhans in Three–Dimensional Matrix Culture," *Cell Transplant.* 3 (5):427–435 (1994).

Chao, S.–H., et al., "Entrapment of Cultured Pancreas Islets in Three–Dimensional Collagen Matrices," *Cell Transplant.* 1:51–60 (1992).

Karhumäki, et al., "An Improved Enrichment Method for Functionally Competent, Highly Purified Peripheral Blood Dendritic Cells and its Application to HIV–Infected Blood Samples," *Clin. Ex. Immunol.* 91:482–488 (1993).

Lu, L., et al., "Propagation of Dendritic Cell Progenitors from Normal Mouse Liver Using Granulocyte/Macrophage Colony–Stimulating Factor and Their Maturational Development in the Presence of Type–I Collagen," *J. Exp. Med.* 179:1823–1834 (1994).

Mactonia, S.E., et al., "Primary Proliferative and Cytotoxic T–Cell Responses to HIV Induced in Vitro by Human Dendritic Cells," *Immunol.* 74:399–406 (1991).

Van den Elsen, J. H. M. et al. J. Immunol. Methods 112: 15–22. 1988.

Shimizu, J. et al. J. Immunol. 155: 4095–4099. 1995.

Steinman, R. Annu. Rev. Immunol. 9:271–296. 1991.

Burtles, S. et al. J. Immunol. 149: 2185–2193. Sep. 1992.

Asthana, D. et al. Transplant Immunol. 1 (4): 282–293. 1993.

Wong, S. et al. Diabetes 44: 326–329. Mar. 1995.

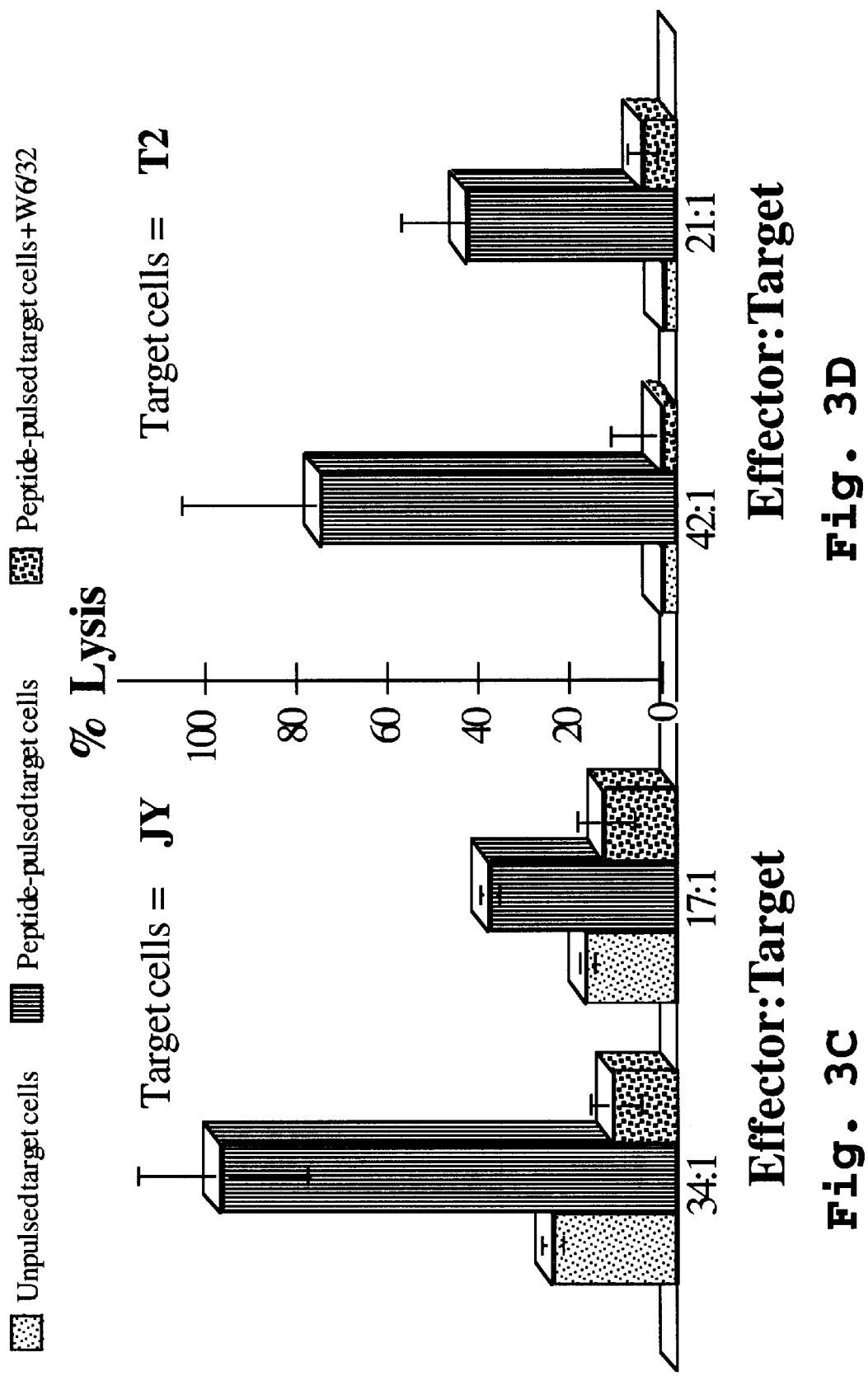

POTENT ANTIGEN PRESENTING CELL COMPOSITION

This invention was made with Government support under grant # 1 U19 AI 36608-01 awarded by the National Institute of Health. Accordingly, the United States Government has certain rights in this invention.

FIELD OF THE INVENTION

The present invention relates to potent antigen-presenting (PAP) cells and in particular, to methods of preparing PAP cells and to a composition containing PAP cells entrapped in a three-dimensional matrix.

REFERENCES

Ausubel, F. M., et al., CURRENT PROTOCOLS IN MOLECULAR BIOLOGY, John Wiley and Sons, Inc., Media Pa.
Brendel, M. D., et al., Cell Transpl. 3:427–435 (1994).
Chao, S- H., et al., Cell Transpl. 1:51–60 (1992).
Elovaara, I., et al., J. Exp. Med. 177:1567–1573 (1993).
Grabbe, S., et al., Immunol. Today 16:117–121 (1995).
Kabel, P. J., et al., Immunobiology 179:395–41 (1989).
Kannagi, M., et al., J. Virol. 66:2928–2933 (1992).
Langer & Bacanti Science 260:920–926 (1993).
Macatonia, et al., Immunology 74:399–406 (1991).
Markowicz, S., and Engleman, E. G., J. Clin. Invest. 85:955–961 (1990).
Mehta-Damani, A., et al., J. Immonol. 153:996–1003 (1994).
Mulligan, R. C. Science 260:926 (1993).
Nair, S., et al., J. Immunol. Meth. 152:237 (1992).
Pope, N. M., et al., Bioconjugate Chem., 4:186–171 (1993).
Reddy, R., et al., J. Immunol. 148:1585 (1992).
Stevens, E. J., et al., J. Immunol. 154:762–771 (1995).
Thomas R., and Lipsky, P. E., J. Immunol. 153:4016–40128 (1994).
Young, J. W., and Steinman, R. M., Cell. Immunol. 111:167–182 (1987).
Zhou, F., et al., J. Immunol. 149:1599 (1992).
Zweerink, H. J., et al., J. Immunol. 150:1763–1771 (1993).

BACKGROUND OF THE INVENTION

Literature reports indicate that different researchers employ labor intensive and highly diverse techniques for isolation and in vitro generation of antigen presenting cells (APC).

Not only are there various types of APC and protocols for isolating them and activating them in vitro cultures, but also within a given APC type there are variations with regard to isolation and activation procedures. For example, in instance of DC as APC, a variety of methodologies have been reported for the isolation of DC (Macatonia, et al., 1991; Markowicz and Engleman, 1990; Young and Steinman, 1987). Moreover, there appear to be significant differences in the characteristics of the final dendritic cell preparation as indicated by differences in cell surface marker expression, leading to the recent consensus that there exist at least three sub-types of DC (Grabbe, et al., 1995; Thomas and Lipsky, 1994).

SUMMARY OF THE INVENTION

The invention includes, in one aspect, a method for obtaining, from a human blood sample, potent antigen presenting (PAP) cells characterized by (i) a phenotype that is positive for surface antigen HLA DR and negative for surface antigens CD3, CD4, CD8, CD14, CD16, and CD20, and (ii) the ability to elicit primary and secondary immune responses when co-cultured with human lymphocytes in culture.

The method includes obtaining from the blood sample, a monocyte-depleted fraction containing peripheral blood lymphocytes and dendritic-precursor cells. This fraction is cultured in a serum-free medium for a period sufficient to produce a morphological change in dendritic-precursor cells to cells having the morphology of dendritic cells. Non-adherent cells are harvested, and the harvested cells are enriched for PAP cells by density centrifugation.

The fraction enriched in peripheral blood lymphocytes and dendritic-precursor cells is preferably obtained by (i) first enriching the blood sample in peripheral blood mononuclear cells by density centrifugation, and (ii) enriching the product of (i) in lymphocytes and dendritic-precursor cells by density centrifugation. The final enriching step is preferably carried out by layering the product of (i) over a separation medium having a density of 1.0650±0.0010 g/mL, and an osmolarity of 300±15 mosm.

Exemplary serum-free media for culturing the cells containing PAP-precursor cells include Dulbecco's Modified Minimal Essential Medium (DMEM):F-12 (1:1), AIM-V or macrophage serum-free medium. Culturing is carried out until dendritic-precursor cells undergo the desired morphological change to dendritic cells, preferably at least about 24 hours.

The method may further include, following the enriching step, contacting the cells in the PAP-enriched fraction with a solid phase conjugated with antibodies against at least one cell surface phenotype marker selected from the group consisting of CD4, CD8, CD14, CD3, CD16, and CD20, and removing cells in the fraction which bind to the solid phase. After this final step, the dendritic cells may constitute more than 50% of the cell fraction.

The method may further include entrapping PAP cells in the enriched fraction in a three-dimensional matrix, such as a collagen-fiber matrix, to preserve the differentiation state and antigen presentation capability of the PAP cells in culture for an extended culture period.

In another aspect, the invention includes a cell composition composed potent antigen presenting (PAP) cells of the type described above entrapped in a three-dimensional matrix, as exemplified by a collagen-fiber matrix.

In a related aspect, the invention includes a method of vaccinating a subject against a tumor or pathogen with a known tumor- or pathogen-specific antigen. The method includes isolating from the subject, a blood-cell fraction enriched for potent antigen presenting (PAP) of the type described above, entrapping the PAP cells in a three-dimensional biocompatible matrix, treating the matrix-entrapped PAP cells with an HLA-binding peptide containing the selected antigen, and exposing the subject's cytotoxic T cells to the matrix.

The exposing step may involve injecting the cell-containing matrix into the subject, or removing cytotoxic T lymphocytes from the patient, contacting the lymphocytes with the matrix in vitro, and returning the contacted lymphocytes to the patient's bloodstream.

These and other objects and features of the invention will become more fully apparent when the following detailed description of the invention is read in conjunction with the accompanying drawings.

BRIEF DESCRIPTION OF THE DRAWINGS

FIG. 3A shows lysis measured on day 34 of the T-cell culture; FIG. 3B shows lysis measured on day 41 of T-cell culture.

FIGS. 3C and 3D show antigen-specific lysis, measured in standard 4 hour $^{51}Cr$ release assay, by cultured T-lymphocytes measured against JY (FIG. 4A) and T2 (FIG. 4B) target cells that had been either (i) unpulsed, (ii) pulsed with the HTLV-1 peptide (SEQ ID NO:1), or (ii) pulsed with the HTLV-1 peptide (SEQ ID NO:1), and then exposed to an antibody (W6/32) directed against an HLA class I antigen.

DETAILED DESCRIPTION OF THE INVENTION

I. Definitions

Figure 1B:
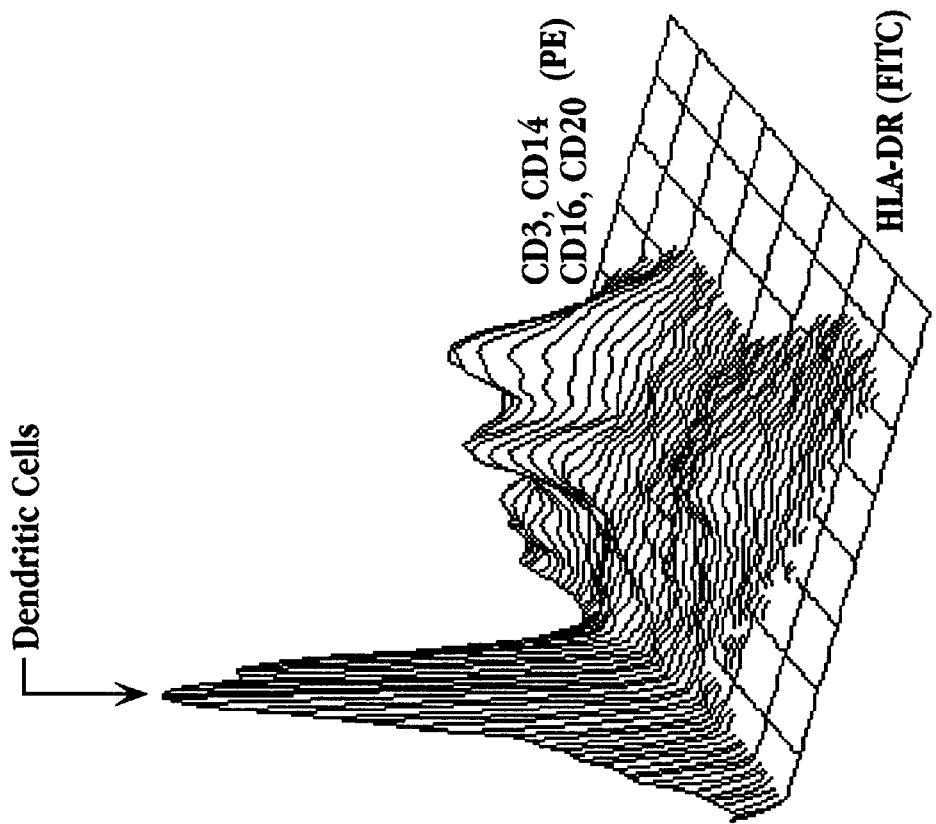
FIGS. 1A and 1B show fluorescence-activated cell sorting (FACS) profiles used to characterize the purity of dendritic cells (DC) in a DC-enriched fraction obtained from the interface of a density centrifugation in MEP following a two day culture of monocyte depleted peripheral blood mononuclear cells. The cells were stained with CD3, CD14, CD16 and CD20 on the PE channel and HLA-DR on the FITC channel. DC stain positively for HLA-DR but are negative for the cell phenotype indicators used on the PE channel (FIG. 1B). IgG2a was used, on both the FITC and PE channel, as the isotype control (FIG. 1A).

Unless otherwise indicated, the terms below have the following meanings:

"Dendritic-precursor cells", or "DPCI", are peripheral blood cells which can mature into dendritic cells under suitable conditions. DPC typically have a non-dendritic morphology and are not competent to elicit a primary immune response as antigen presenting cells.

"Dendritic cells", or "DC" are matured DPC, which are negative for expression of CD3, CD4, CD8, CD14, CD16 and CD20, positive for expression of HLA-DR (i.e., class II MHC). Dendritic cells typically have a dendritic cell morphology—that is, they are large veiled cells which extend dendrites when cultured in vitro.

"Potent antigen presenting (PAP) cells" are dendritic cells which, after being pulsed with an antigen, can activate naive $CD8^+$ cytotoxic T-lymphocytes (CTL) in a primary immune response.

II. Overview of Invention

The present invention relates to the isolation, enrichment, culture and immunotherapeutic or immunoprophylactic applications of potent antigen presenting (PAP) cells, a class of dendritic cells (DC) capable of eliciting primary immune responses in naive CD8+ cytotoxic T-lymphocytes. The PAP cells are obtained from peripheral blood using multiple density gradients generated from a single density gradient material. The isolation procedure can be completed in two days and is preferably performed entirely under serum-free conditions. The percent of PAP cells in enriched, isolated fractions may be further increased by depleting contaminating cells using, for example, solid-phase antibody-based negative depletion. Further, the isolation, enrichment and culture procedures described herein may be conveniently performed in a closed device/kit configuration.

The PAP cells present in enriched fractions are capable of eliciting both primary and secondary immune responses when co-cultured with human lymphocytes in vitro, and may be used in a number of applications. For example, they may be used to generate antigen-specific cytotoxic T-lymphocytes (CTL) having activity directed against major histocompatibility complex class I (MHC-I) restricted peptides from tumor- and virus-specific antigens, for use as immunotherapy compositions.

Another aspect of the invention is directed to maintenance of the differentiated function of PAP cells by culturing them in a three-dimensional, porous, biocompatible matrix. According to the teachings herein, culturing the cells in such a matrix reduces or eliminates the need for exogenous cytokine supplementation, and is effective to preserve the differentiated state of the cells for at least 12 days. Such compositions may be used, for example, to immunize individuals against selected antigens.

III. Cell Fraction Enriched for PAP Cells

A. Preparation

According to the methods of the present invention, a fraction enriched in PAP cells may be obtained by (i) obtaining, from a human blood sample, a monocyte-depleted cell fraction containing peripheral blood lymphocytes and dendritic-precursor cells, (ii) culturing the cell fraction in a serum-free medium for a period sufficient to produce a morphological change in dendritic-precursor cells to cells having the morphology of dendritic cells, (iii) harvesting non-adherent cells produced by the culturing, and (iv) enriching the portion of dendritic cells in the harvested cells by density centrifugation, to obtain a fraction enriched in PAP cells.

Although the exemplified method achieves step (i) by density centrifugation, as detailed below, it will be understood that other approaches may be used to obtain such a monocyte-depleted cell fraction. For example, counterflow elutriation centrifugation (Kabel, et al.) may be employed to remove the monocytes.

In one embodiment, the fraction enriched in PAP cells is obtained as detailed in Example 1, below. This procedure is based on a combination of density based separation of cell types and differentiation-induced changes in densities of cell types following in vitro or ex vivo culture. A DPC-containing sample, such as a sample from human peripheral blood (e.g., buffy coats) is diluted with a suitable buffer, such as $Ca^{++}/Mg^{++}$ free phosphate buffered saline, and layered onto a density gradient material or separation medium (preferably having a density of about 1.0770+/−0.0010 and an osmolarity of about 310+/−15) and centrifuged. Exemplary density gradient materials for this step include the silica-based FEP (described in Materials and Methods, below), made from "PERCOLL" (Pharmacia LKB, Uppsala, Sweden), and Lymphoprep (Nycomed Laboratories, Oslo, Norway). The separations can be carried out either in any suitable tube, such as an ordinary 50 mL centrifugation tube.

The interface of the solutions in the centrifuged tubes contains peripheral blood mononuclear cells (PBMC), which are harvested, e.g., by pipeting the cells from the interface. The PBMC are then resuspended in a suitable buffer, such as D-PBS, and centrifuged to remove platelets (which remain in the supernatants). Platelet-depleted PBMC are again resuspended in a suitable buffer, such as D-PBS, and layered on a density gradient material or separation medium (preferably having a density of about 1.0650+/−0.0010 and an osmolarity of about 300+/−15) and centrifuged. An exemplary density gradient material for this step is the silica-based MDP, also made from "PERCOLL" as described below.

The cells at the interface of the two solutions are primarily monocytes, while those in the pellet are primarily lymphocytes. The monocyte (interface) fraction may be resuspended in a suitable culture medium, such as cold pooled human AB serum to which an equal volume of 80% AB serum 20% dimethyl sulfoxide (DMSO) is added dropwise, and frozen until needed.

The pellet cells comprise a monocyte-depleted cell fraction containing peripheral blood lymphocytes and dendritic-precursor cells. These cells are harvested, washed, e.g., with D-PBS by centrifugation at room temperature, and resuspended in a suitable culture medium, inoculated into tissue culture flasks and cultured in a humidified incubator for at least 24 hours, preferably about 40 hours. The culturing period is sufficiently-long to produce a morphological change in the dendritic-precursor cells (DPC) to cells having the morphology and characteristics of dendritic cells (DC).

This morphological change may be detected using, for example, photomicroscopy. DC are large sized veiled cells which, when cultured in vitro, typically extend cytoplasmic processes from the cell surface. A practical consequence of this morphological change (i.e., an indicator that it has occurred) is a slight change in the cells' density, such that they become less dense. As a result of this change in density, the DC cells can be isolated, for example, from the interface following density centrifugation using a density gradient material or separation medium having a density of about 1.0800±0.0010 and an osmolarity of about 540±25, or alternatively, a density of about 1.0550±0.0010 and an osmolarity of about 290±15, as described below.

According to the methods of the present invention, the culture medium used in the DC isolation procedure, and particularly in the culturing step described in the above paragraph, is preferably serum-free. Experiments performed in support of the present invention and detailed in Example 1 and Table 2 herein demonstrate that the use of serum-free media in the isolation procedure and in the culturing step results in a superior purity of DC cells obtained in the final DC (and PAP)-enriched cell fraction.

Serum-free media which resulted in improved purity of subsequently-harvested DC cells included DMEM/F-12, Enriched Monocyte SFM, AIM-V and Enriched AIM-V. All of these are available from Gibco/BRL Life Technologies, Gaithersburg, MD. Other serum-free media may also be employed in the practice of the present invention. Examples include Hybridoma Serum-Free Medium (Gibco), Protein-Free Hybridoma Medium (Gibco), Iscove's Modified Dulbecco's Medium (IMDM; Sigma), and MCBD medium (Sigma).

Following the culture period, non-adherent cells are harvested, for example, by gentle pipeting of the medium to dislodge cells that had settled but had not firmly adhered to the culture dish. The harvested cells are washed and resuspended at a concentration of $2-5 \times 10^6$ cells/mL in a suitable culture medium, such as one of the serum-free culture media described above. The resulting cell suspension is enriched by layering onto a density gradient material or separation medium (preferably having a density of about 1.0800+/−0.0010 and an osmolarity of about 30+/−15) and centrifuged. Exemplary density gradient materials for this step include the silica-based MEP, made from "PERCOLL", as well as ~14.5% Metrizamide.

MEP is a hyperosmotic medium. A similar separation may be achieved using an isosmotic medium, with the density empirically adjusted downward to result in similar separation characteristics. The density is lower in the isosmotic medium because cells in isosmotic media do not lose water and shrink (i.e., become more dense) the same way they do in hyperosmotic media.

An exemplary isosmotic density gradient formulation, or separation medium, useful for obtaining a PAP cell-enriched fraction is IOMEP (Isosmotic MEP). IOMEP has a density of 1.0550±0.0010 g/mL, an osmolarity of 290±15 mosm and a pH of 7.4±0.2. It is functionally equivalent to MEP, in that it results in similar isolation yields and purities for PAP cells as are obtained on using MEP. Moreover, the function of PAP cells in the interface cell fraction, measured in terms of generation of an immune response, is similar irrespective of whether the cells were isolated on MEP or IOMEP.

Accordingly, isolation of PAP cells is dependent on the separation characteristics of the density gradient used, which in turn depends on the physical attributes such as the density, osmolarity and pH of the gradient material used. It will be appreciated that any separation medium having a combination of these characteristics such as presented above is effective for obtaining a cell fraction enriched for PAP cells.

The fraction present at the interface following the above centrifugation is enriched in DC and PAP cells. The purity of DC in this fraction may be quantified using, for example, flow cytometry cell sorting (FACS) analysis. DC, including the DC purified by the methods of the present invention, are typically negative for cell phenotype markers CD3 (T-cells), CD14 (monocytes), CD16 (NK cells) and CD20 (B-cells) and positive for HLA class II expression, as evidenced by positive staining for HLA-DR (Macatonia, et al., 1991; Markowicz and Engleman, 1990; Young and Steinman, 1987).

Figure 1A:
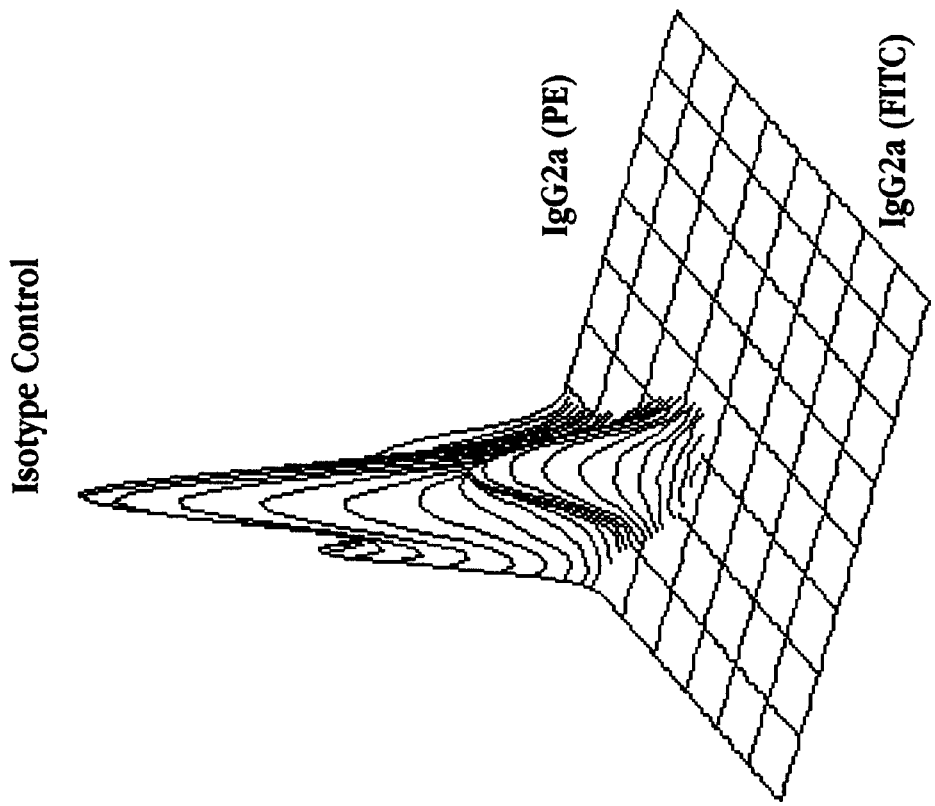

FIG. 1 shows a representative FACS profile of the DC enriched fraction obtained using methods of the present invention. The DC purity in this profile is approximately 16.0%. On average, $0.9 \pm 0.7 \times 10^6$ (meanjsd) DC with a purity of $15.4 \pm 10.1\%$ (meanjsd) were obtained from one unit of blood (n=60). The contaminating cells were mainly T-cells, NK-cells, monocytes and B-cells, in order of magnitude of contamination.

If additional purification is desired, the DC and PAP-enriched fraction may be subjected to additional purification steps. For example, antibodies directed against antigens not expressed on DC, such as CD3, CD14, CD16, and/or CD20, may be immobilized on a solid support and used to remove, or "negatively deplete", contaminating cells. Such additional purification can result in further enrichment of DC cells, such that the DC cells constitute over 50% of the cells in the fraction, without appreciable loss of PAP cells.

Negative depletion experiments performed in support of the present invention demonstrated that incubation of the MEP interface fraction with beads conjugated with monoclonal antibodies for the cell surface phenotype markers CD4, CD8 and CD14 resulted in an additional ~3-fold purification (i.e., ~50% purity of PAP cells) without appreciable loss of cell yield. Protocols for the conjugation of antibodies to beads, and for the use of such conjugated beads for negative depletions, are well known (e.g., Pope, et al.).

The degree of enrichment of PAP cells in the final fraction may be determined using, for example, limiting dilution analysis in a CTL-activating assay. The PAP-enriched fraction is pulsed with an antigen (e.g., as in the Materials and Methods), and serial dilutions of the pulsed fraction are made. The dilutions are then used to stimulate expansion of T-cells, e.g., as detailed in Example 2. The relative number of PAP cells expressing the antigen in association with an MHC and capable of activating T-cells can be estimated based on the most diluted sample that results in T-cell expansion.

According to the present invention, PAP cells, which constitute a portion or all of the DC cells isolated by the methods of the present invention, are effective to result in the generation of a primary immune response mediated by CTL, after the PAP cells are pulsed with an antigen.

The yield and purity of PAP cells in the final fraction was evaluated as a function of the number of cells introduced into the monocyte-depleted cell fraction culture (inoculum cell concentration), as well as medium and serum composition. Results of experiments performed in support of the present invention indicate that optimal PAP cell yield and purity may be obtained if the culture is inoculated with about $2.0–10.0 \times 10^6$ MDP pellet cells per mL of culture medium.

In addition to the above serum supplemented medium, a variety of serum-free media were evaluated for DC yield and purity as described above and in Example 1, below. Results of these experiments suggested that the addition of serum had detrimental effects on both the yield and purity of PAP cells. In two of the serum-free media analyzed, AIM-V and Macrophage serum free medium (Macrophage-SFM), the yield and purity of PAP cells in the MEP interface was approximately two fold higher. These results indicate that the entire procedure of isolation and enrichment of PAP cells can be performed under entirely serum-free conditions. Due to the advantages of defined media from reproducibility as well as regulatory and product-development perspectives, these results have significant implications.

The total yield of PAP cells is calculated based on the evaluation of total cell number in the final (e.g., MEP) interface fraction and the purity of PAP cells in that fraction. However, in the procedure detailed above, the PBMC are separated (e.g., over an MDP gradient), and only the pellet fraction of the MDP gradient is used to isolate PAP cells following culture. The culture phase allows for the maturation of the PAP progenitor cells into differentiated PAP cells which are subsequently separated on the MEP gradient.

In order to optimize the yield of PAP cells, the percentage of PAP progenitor cells which were lost to the MDP interface was quantitatively assessed. The PAP cell isolation procedure was performed with and without separating the PBMC on the MDP gradient. The results indicate that approximately 30% of PAP cell progenitors are lost in the MDP interface fraction. Thus, to increase the total yield of PAP cells, it would appear that one should not separate the MDP interface cells. However, in instances when the MDP interface cells were not separated, although the yield of DC was approximately 30% greater, the purity of PAP cells was reduced by an order of magnitude.

The apparent reason for the reduction in the PAP cell purity is that following the 40 hour culture, all the cells which normally would have been separated in the EDP interface (which is approximately one-fifth to one-third of the total number of PBMC) co-purify with the PAP cells in the MEP interface. Accordingly, the subsequent enrichment for obtaining high purity PAP cells is exhaustively more involved.

B. Characterization of Enriched Cell Fraction

DC in the enriched cell fraction typically have a dendritic morphology when cultured in vitro. Further, as described above, the cells are typically negative for cell surface markers CD3, CD4, CD8, CD14, CD16, and CD20, and positive for MHC class II, as evidenced, for example, by HLA-DR expression.

PAP cells in the fraction have the characteristics of the DC cells stated above, as well as the ability to stimulate a primary immune response mediated by MHC class I restricted CTL. This functional competence was assessed by measuring proliferative response in an allogeneic T-cell stimulation setting as detected by tritiated thymidine incorporation and by generation of peptide-specific CTL (Examples 2 and 3).

C. Pulsed Cells

Several methods may be used to pulse PAP cells with antigen, to make them effective or competent to activate a desired subset of CTL. For example, experiments detailed herein demonstrate that the cells may be exposed to antigenic peptides, and that these peptides can be processed through the "endogenous" class I pathway such that they are presented in association with MHC class I molecules, and accordingly are able to activate CD8+ CTL.

It had been demonstrated that, in addition to peptides, certain proteins may be introduced to PAP cells such that the proteins are processed through the MHC class I, as opposed to class II, pathway (see, for example, Mehta-Damani, et al.). In particular, the incorporation of antigens into liposomes has been used to accomplish such targeting (e.g., Nair, et al., Reddy, et al., Zhou, et al.).

Of course, selected antigens can be introduced to PA cells by transfecting the cells with expression vectors containing genes encoding such antigens. Transfection of PAP cells with a gene encoding a desired antigen is an effective way to express the antigen in association with the class I MHC. Any of a variety of known methods (see, for example, Ausubel, et al., Mulligan) may be used for such transfections, including $CaPO_4$ precipitation, lipofection, naked DNA exposure, as well as viral vector-based approaches, such as retroviral, adenoviral, AAV, and vaccinia virus vectors.

III. Biomatrix Composition

Isolated PAP cells in culture typically lose the cytoplasmic processes extending from the cell surface as well as their ability to effectively present antigens to lymphocytes for generation of primary and secondary immune responses. According to one aspect of the invention, PAP cells (pulsed or unpulsed) can be maintained in a desired (e.g., active) state by culturing the cells in a three-dimensional matrix. Matrices which may be suitable for such culturing are reviewed by Langer & Bacanti. They include hydrogels, agarose (Brendel, M. D., et al.), and collagen (Chao, S- H., et al.) matrices effective to entrap the cells and provide them with a scaffold on which to grow.

Such a gel or matrix is preferably stable under the conditions used for culturing. The matrix may be used to maintain a particular morphology, expression pattern or functional properties of the cells.

Experiments detailed in Example 7 describe the culturing of cells in a three-dimensional cross-linked collagen matrix. Isolated MEP interface fraction, containing PAP cells, was mixed with a solution of collagen type I monomers. This cell-collagen suspension was induced to in situ polymerize following a step change in pH and temperature, thus effectively entrapping the DC cells in a highly porous three dimensional matrix of collagen fibers. Morphological observation of cells entrapped in collagen indicated maintenance of differentiated morphology of PAP cells following prolonged long-term culture over 12 days. Evaluation of cells released on the FACS, following digestion of the collagen matrix after 12 days of culture, indicated majority of the viable cells exhibited phenotype markers indicative of their being DC cells.

The entrapped DC cells were pulsed with HLA-A*0201 binding peptide and used to generate antigen-specific $CD8^+$ T-lymphocytes. The generated CTL demonstrated peptide-specific lysis of target cells. These results indicate the ability to maintain differentiated state and antigen presentation capability of PAP cells following collagen-entrapped cultures.

These results have significant implications for the design and application of implantable or extracorporeal devices and/or systems for immunomodulatory therapies. For example, a patient's autologous DC cells can be isolated and entrapped in a three-dimensional system which is subsequently pulsed with antigen or peptide and used as a vehicle for implantable or extracorporeal vaccination against native antigens to treat tumor or viral diseases.

Cell/matrix compositions of the present invention preferably contain a percentage of DC and/or PAP cells that is sufficient to stimulate a primary or secondary immune response when the composition is contacted with lymphocytes. Typically, the entrapped cell contain at least 10% DC, preferably at least 50% DC.

The PAP cells in the matrix may be modified for presentation of a selected antigen, i.e., they may be "pulsed" with a peptide or protein, or transfected with a gene encoding a selected antigen. The antigen may be any antigen against which it is desired to mount an immune response, such as a tumor or viral antigen.

IV. Utility

A. Fraction Enriched for PAP Cells

The multiple density gradients generated from a single density gradient material employed in the isolation of PAP cells may be used in a simple, closed device or kit. The PAP cells isolated using methods of the present invention may be used in a number of applications. One of the useful features of the PAP cells isolated by the methods of the present invention is that they are able to present antigens for the induction of primary ($CD8^+$ CTL-mediated) T-cell responses, as well as being able to activate $CD4^+$ T cell proliferative responses in cases where the donor of the T-cells had been previously exposed to the antigen. As such, the PAP cells are universally-useful antigen-presenting cells and can be employed in a wide range of immunotherapeutic and immunoprophylactic applications involving generation of primary and secondary immune responses.

The cells can be used, for example, in direct in vivo administration, ex vivo somatic therapy, in vivo implantable devices and ex vivo extracorporeal devices. They can also be employed in the screening of antigenicity and immunogenicity of peptide epitopes from tumor- and virus-specific antigens. PAP cells treated or pulsed with appropriate antigens can be used as potent vaccine compositions, for example against pathogenic viruses or cancerous tumors.

In certain cases, it may be advantageous to use cells obtained from one individual to treat a condition in a second individual. For example, HIV-infected individuals with AIDS are often not able to mount antiviral T-cell responses. In such cases, CTL can be isolated from healthy HLA-matched individuals, such as siblings, be stimulated or primed with antigen-pulsed DC in vitro, expanded, and administered back to the HIV-infected individuals.

The isolated DC cells may also be used, for example, in gene therapy applications, such as transfection of the cells so that they constitutively express desired antigens/gene products for therapeutic applications.

B. Matrix composition

The differentiated function of the PAP cells was maintained by culturing them in a three-dimensional, porous, biocompatible matrix without need for exogenous cytokine supplementation. As detailed above (e.g., Example 7), PAP cells cultured in a collagen matrix exhibited ability to elicit primary and secondary immune responses, and to maintain their differentiation state and antigen presentation capability for at least 12 days. These characteristics make the cell/matrix composition useful in a number of applications.

DC and PAP cells (e.g., cells isolated according to the methods of the present invention) cultured in a three-dimensional matrix may be used in application where it is desired to have a stable supply of cells in a specific state over the course of several days. For example, a three-dimensional matrix containing DC and PAP cells may be employed in implantable and/or extracorporeal devices/systems for use in immunomodulatory therapies. A patient's autologous PAP cells may be isolated and entrapped in a three-dimensional matrix such as described herein. The matrix may then be pulsed with antigen or peptide and used as a vehicle for implantable or extracorporeal vaccination against native antigens (e.g., extracorporeal activation of lymphocytes) to treat patients with tumor or viral diseases.

Immunotherapies for individuals with defective lymph nodes are also contemplated. In such applications, a PAP cell-containing matrix is implanted into an individual to serve as an "artificial" lymph node.

An exemplary use of the cell/matrix compositions detailed herein is for immunizing a subject against a tumor or pathogen having a known tumor- or pathogen-specific antigen. In such an application, a blood-cell fraction enriched for PAP is isolated, e.g., as described above, and the PAP cells are entrapped in a three-dimensional biocompatible matrix, such as a hydrogel, collagen gel or agarose. The cells are treated or "pulsed", either before or after the entrapping, with a selected antigen, in a manner effective to result in presentation of the antigen in association with class I MHC.

If the treatment entails transforming the cells with a vector containing a gene capable of expressing the antigen, the treatment is typically done before entrapping, and transfected cells are selected (using standard methods, e.g., Ausubel, et al.) for subsequent entrapping. Alternatively, if the treatment consists of exposing the cells to antigenic protein or peptide, the treatment may be done after the cells are entrapped.

Following the treatment of the PAP cells, the cells express the selected antigen in association with class I MHC, and are thus effective to stimulate an immune response when contacted with lymphocytes (e.g., a primary immune response when contacted with naive CTL. The treated cells entrapped in the matrix are then contacted with, or exposed to, the subject's lymphocytes. This exposure has the effect of stimulating or activating the lymphocytes such that they are capable of generating a primary or secondary immune response.

In cases where the exposing is done extracorporeally, the lymphocytes (e.g., CTL) are removed from the subject and exposed to the PAP cells in the matrix. The lymphocytes, many of which have been activated by the entrapped PAP cells, are injected back into the subject, where they result in the mounting of an immune response. Alternatively, the matrix containing the treated PAP cells can be injected or implanted into the subject, such that the contacting or exposing of the lymphocytes to the entrapped PAP cells occurs in the subject, and lymphocytes activated by such contacting can directly precipitate the mounting of an immune response.

The following examples illustrate, but in no way are intended to limit the present invention.

Materials and Methods

Media

AB Culture Medium: Basal RPMI-1640 medium (Gibco Laboratories, Grand Island, NY) supplemented with 2.0 mM L-Glutamine (Gibco Laboratories, Grand Island, N.Y.) and 5% pooled human AB serum (Irvine Scientific, Santa Ana, Calif.).

Formulation of Density Gradients

Density gradients were prepared using "PERCOLL" (Pharmacia LKB, Uppsala, Sweden), a silica-based density gradient material (separation medium) with a density of about 1.129±0.001 g/mL, an osmolarity of about 15±15 mOsm and a pH of about 9.0±1.0. A stock isotonic "PERCOLL" (SIP) density gradient solution was prepared by mixing the "PERCOLL" with 10× calcium/magnesium-free phosphate buffered saline (D-PBS) (Gibco Laboratories, Grand Island, N.Y.) at a ratio of 1:9 (v/v). The following density gradient solutions were prepared by mixing the SIP solution with 1× D-PBS or 2.66× D-PBS. 2.66× D-PBS was made by mixing 10× D-PBS with and endotoxin-free (LAL) water (Biowhittaker, Walkersville, Md.) in a 0.2086±0.0010 to 0.8083±0.0010 ratio on a weight basis. The abbreviations are as follows: FEP—Ficoll Equivalent Percoll; MDP—Monocyte Depletion Percoll, MEP—Metrizamide Equivalent Percoll, and IOMEP—Iso-Osmolar Metrizamide Equivalent Percoll.

TABLE 1

| Density Gradient Solution | Density (g/mL) | Osmolarity (mOsm/kg H$_2$O) | pH |
|---|---|---|---|
| SIP | 1.2210 ± 0.0010 | 280 ± 15 | 7.4 ± 0.2 |
| FEP | 1.0770 ± 0.0010 | 310 ± 15 | 7.4 ± 0.2 |
| MDP | 1.0650 ± 0.0010 | 300 ± 15 | 7.4 ± 0.2 |
| MEP | 1.0800 ± 0.0010 | 540 ± 25 | 7.4 ± 0.2 |
| IOMEP | 1.0550 ± 0.0010 | 290 ± 15 | 7.4 ± 0.2 |

The solutions were prepared according to the following formulas, where $\rho$ is density, v is volume, w is weight and x is the volume fraction of individual components in a mixture (m) of components (1) and (2), such that $x_1+x_2=1$, $v_1+v_2=v_m$, and $w_1+w_2=w_m$. Note that the subscripts in each case refer to either component (1), component (2) or the mixture (m). Component (1) was typically SIP and component (2) was either 1× D-PBS (density of 1.0064±0.0010) or 2.66× D-PBS (density of 1.0169±0.0010):

$$x_1 = \frac{\rho_m - \rho_2}{\rho_1 - \rho_2} \qquad x_2 = 1 - x_1$$

The formulas were entered into a spreadsheet program ("EXCEL", Microsoft Corp., Redmond, Wash.) to facilitate repetitive calculations of the weight of each component to generate mixtures having desired densities.

The formulated solution was characterized by measuring its (i) density on a densitometer (Model # DMA-48, Anton Paar, Ashland, Va.), (ii) osmolarity on a freezing point depression osmometer (Model #2400, Fiske Instruments, Norwood, Mass.) and (iii) pH using a pH meter (Model #345, Corning, Corning, N.Y.). Sterilized 1.0 M sodium hydroxide and 1.0 M hydrochloric acid solutions were used to correct the pH. Density and osmolarity were adjusted either by addition of SPI or PBS (1×, 2.66× or 10×, as required), respectively, to increase the values, or by addition of sterile water to decrease the values, to obtain a density gradient solution within the acceptable range of solution characteristics (see Table 1, above).

Elicitation and Expansion of Antigen-Specific T-Lymphocytes

Antigen-specific cytotoxic T-lymphocytes were elicited essentially as described by Mehta-Damani, et al., 1994. Three HLA-A*0201 binding peptides were used to elicit antigen-specific cytotoxic T-lymphocytes (CTL). The first (SEQ ID NO:1) corresponds to amino acids 11–19 of the Tax gene product of human trophic leukemic virus 1 (HTLV-1; Elovaara, et al., 1993; Kannagi, et al., 1992; Zweerink, et al.), the second (SEQ ID NO:2) corresponds to amino acids 27–35 of the MART-1 antigen expressed on melanoma cells (Stevens, et al.) and the third (SEQ ID NO:3) corresponds to amino acids 464–472 of human immunodeficiency virus (HIV) reverse transcriptase in the polymerase gene. All peptides were synthesized by Bachem Laboratories (Torrance, Calif.).

Stock solutions were prepared by dissolving the peptides in sterile filtered 1.0% acetic acid solution in LAL water (BioWhittaker, Walkersville, Md.) at a concentration of about 1 µg/ml. Isolated DC enriched cell fraction was resuspended in 1.0 mL of basal RPMI-1640 and incubated with 1–5 µg/mL β2-microglobulin (Sigma Chemical Company, St. Louis, Mo.) and 1–5 µg/mL peptide at 37° C. for 1–2 hours. Following the incubation, peptide-pulsed DC were washed to remove excess peptide and mixed with autologous T-lymphocytes (14.5% metrizamide pellet cells) at a ratio of approximately 10:1 to yield a cell concentration of 1.0×10$^6$ cells/mL in AB Culture Medium supplemented with 4.0 U/mL of human recombinant IL-2 (Gibco Laboratories, Grand Island, N.Y.). After 3 days of culture the IL-2 concentration was increased to 20.0 U/ML. The T-lymphocytes were restimulated on a weekly schedule using autologous peptide-pulsed monocytes at a ratio of 10:1. During restimulation, the IL-2 concentration was decreased to 4.0 U/mL and was subsequently increased to 20.0 U/mL after 3 days of culture following each restimulation. CTL cultures were typically expanded for 3–4 weeks before evaluation of antigen-specific target cell lysis.

Cell-Mediated Cytotoxicity Assay

Cell-mediated cytotoxicity assays were performed using a standard 4 hour $^{51}$Cr release assay. An epstein barr virus (EBV)-transfected human B-cell line, JY, and an established human T-cell line with dysfunctional transport associated protein-1 (TAP-1) mutation resulting in presence of unoccupied HLA class I molecules on the cell surface, T2, were used as target cells for the cytotoxicity assays. Both JY and T2 cells can be obtained from the American Type culture Collection (ATCC, Rockville, Md.), and were maintained in tissue culture flasks using AB Culture Medium.

The assay plates were prepared by making six serial dilutions, 1:2, of effector CTL in a final volume of 100 µL/well. Wells used for spontaneous release (background radioactive leakage) contained 100 µL/well of culture medium with no effector CTL. Wells used for measurement of maximal release (maximal $^{51}$Cr incorporated into target cells) contained 50 µL culture medium and 50 µL 1.0% Triton X-100 (Sigma Chemical Company, St. Louis, Mo.) in LAL water.

The target cells were pulsed with peptide as described above for DC. Non-peptide-pulsed target cells and irrelevant peptide-pulsed target cells were used as controls. Target cells were washed and resuspended in 100 µL of AB serum and incubated with 100 µL of $^{51}$Cr (NEN DuPont, Wilmington, Del.; stock concentration=1.0 mCi/mL) for 2 hours at 37° C. Excess unlabeled $^{51}$Cr in the supernatant was washed off by three sequential centrifugal washing steps in AB Culture Medium (600× g, 5 minutes, room temperature). Radiolabeled cells were subsequently resuspended in AB Culture Medium at a concentration of 40,000 cells/mL; 50 µL of this suspension was added to each well (2,000 cells/well) in the 96-well assay plate containing known concentrations of effector CTL.

The plates were incubated at 37° C. for 4 hours in a 5% $CO_2$ incubator. Following the incubation, the cells were centrifuged and pelleted. One hundred µL of supernatant from each well was transferred into correspondingly-labeled wells in T-trays containing 200 µL of scintillation fluid. The T-trays were sealed and $^{51}$Cr released into the supernatant was measured on a Beta-plate counter in calculated counts per minute (CCPM). The assay was set up to measure three replicate wells at each effector:target ratio for each target type. From obtained measurements, % lysis was calculated as:

$$\% \text{ Lysis} = 100 * \frac{(\text{CCPM at measured effector:target ratio} - \text{CCPM for spontaneous release})}{(\text{CCPM for maximal release} - \text{CCPM for spontaneous release})}$$

To assess whether observed lysis was HLA class I restricted, a monoclonal antibody to HLA class I, W6/32, was added to peptide-pulsed target cells at a concentration of 10–30 µg/mL to block HLA class I sites on the target cells.

Flow Cytometry

FACS analysis was done on a FACScan flow cytometer (Becton Dickinson, San Jose, Calif.) connected to a Hewlett-Packard HP-9000 computer (Hewlett-Packard, Palo Alto, Calif.) running "LYSIS II" software (Becton Dickinson). All monoclonal antibodies used for analysis and their respective isotype controls were purchased from Becton Dickinson. Briefly, approximately 100,000 cells were preincubated in each well of a 96-well plate with 50 µl of rabbit serum (Sigma Chemical Company, St. Louis, Mo.) in a final volume of 150 µL for 15–20 minutes at room temperature to block non-specific sites for antibody binding. Ten µL of desired FITC or PE-tagged monoclonal antibody were then added to the wells and the 96-well plate was incubated in the dark at 4° C. for 30 minutes.

The plate was then centrifuged to pellet cells and supernatant was aspirated off to remove unbound antibody. Pelleted cells were resuspended in 100 µL of D-PBS supplemented with 5% human AB serum, fixed and counterstained by addition of 100 µL of 1.0% paraformaldehyde (Sigma Chemical Company, St. Louis, Mo.) supplemented with 2.0 µg/mL of LDS-751 (Molecular Probes, Eugene, Oreg.). LDS-751 fluoresces in the far-red spectrum (PerCP region—detected by FL3 fluorescence channel on the FACScan) and counterstains cells, allowing for distinction between non-nucleated cell (non-staining), nucleated viable cell (weakly staining) and nucleated non-viable cell (very bright staining) populations.

EXAMPLE 1

Isolation of Dendritic Cells and T-Lymphocytes

Buffy coats prepared from one unit of blood from HLA-A*0201 positive volunteer healthy donors were obtained from the Stanford University Blood Center (Stanford, Calif.). Cells were harvested from the leukopacs, diluted to 60 mL using $Ca^{++}/Mg^{++}$ free phosphate buffered saline (D-PBS; Gibco Laboratories, Grand Island, N.Y.) and layered over two 15 mL columns of FEP solution, or alternatively, Lymphoprep (Nycomed Laboratories, Oslo, Norway), in 50 mL centrifuge tubes. The tubes were centrifuged at 1000× g for 35 minutes at room temperature. The centrifuge run was allowed to stop without braking and the peripheral blood mononuclear cells (PBMC), present at the interface, were harvested.

PBMC were resuspended in D-PBS, centrifuged once at 650× g for 10 minutes and twice more at 200× g for 5 minutes to remove platelets. Platelet-depleted PBMC were resuspended in 60 mL of D-PBS, layered on top of two columns of 15 mL of MDP (about 50% "PERCOLL") and centrifuged at 650× g for 25 minutes at 4° C. without braking. The MDP interface (primarily monocytes) and MDP pellet cells (primarily lymphocytes) were harvested and washed with D-PBS by centrifugation at room temperature (once at 650× g for 10 minutes and twice thereafter at 200× g for 5 minutes).

In instances where the PAP cells were used to generate peptide-specific CTL for purposes of elucidating their antigen presentation function, the MDP interface fraction (mostly monocytes) was resuspended in cold pooled human AB serum (Irvine Scientific, Santa Ana, Calif.) to which an equal volume of 80% AB serum 20% dimethyl sulfoxide (DMSO) (Sigma Chemical Company, St. Louis, Mo.) was added dropwise. The resulting cell suspension was aliquoted into cryovials and frozen in liquid nitrogen. The monocytes were used for restimulation of CTL for expansion as described in Example 2, below.

Figure 9:
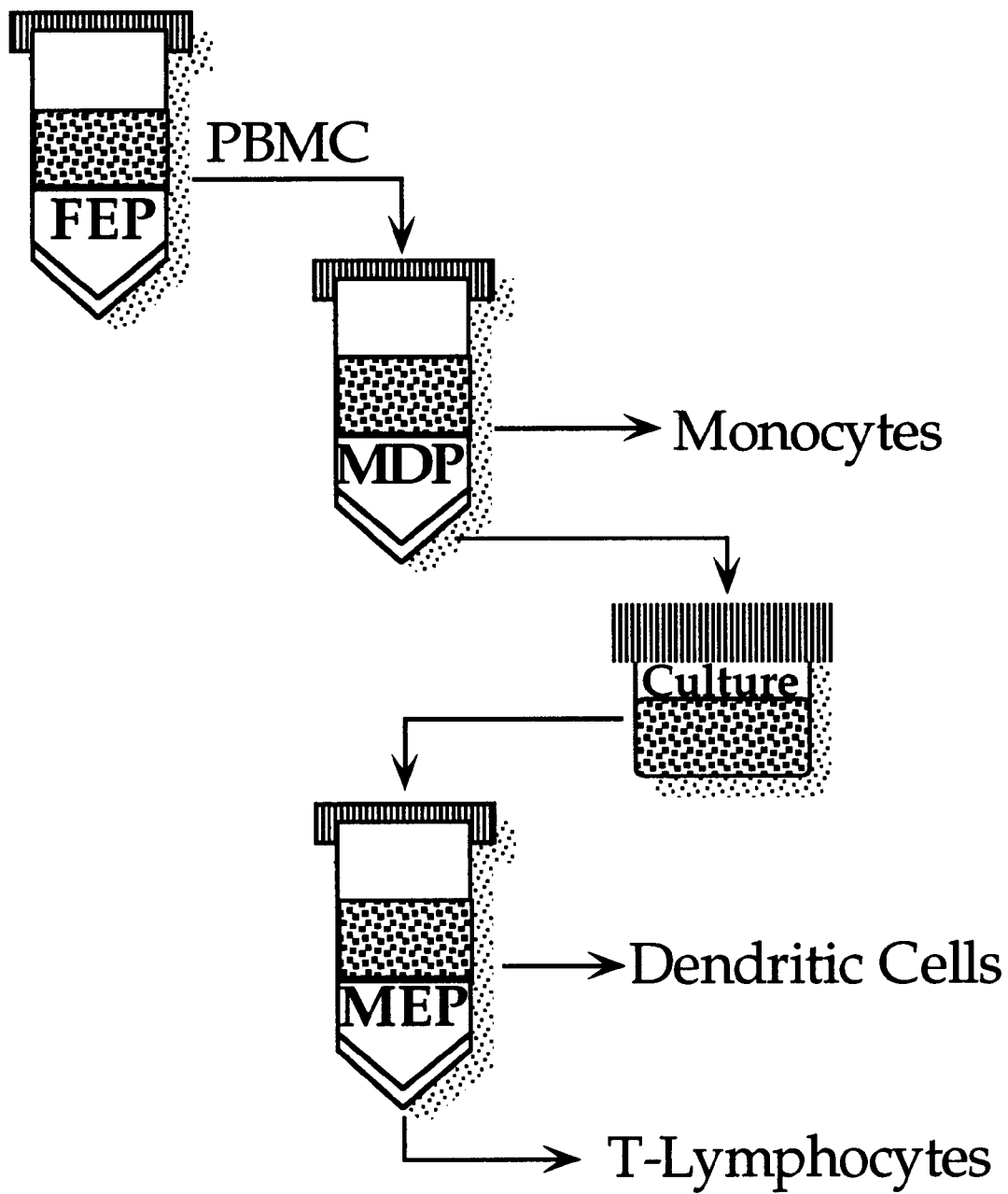
FIG. 9 shows a schematic summary of one embodiment of the PAP cell isolation method of the invention.

The MDP pellet fraction was resuspended in 100 mL of AB Culture Medium, inoculated into two T-75 tissue culture flasks and cultured in a humidified 5% $CO_2$ incubator for 40 hours. Following the incubation, the non adherent cells were harvested by moderate pipeting, washed and resuspended at a concentration of 2–5×10$^6$ cells/mL in AB Culture Medium. The cell suspension was overlayered over four columns of 4.0 mL separation medium (MEP, IOMEP or ~14.5% Metrizamide (Sigma Chemical Company, St. Louis, MO)), in AB Culture Medium and centrifuged at 650× g for 20 minutes at room temperature without braking. A schematic summary of the protocol detailed above is shown in FIG. 9.

The interface and pellet cells were harvested and washed in AB Culture Medium by centrifugation once at 650× g for 10 minutes and twice thereafter at 200× g for 5 minutes each at room temperature. The yield and viability of both cell fractions was estimated by counting on a hemocytometer using trypan blue exclusion.

The purity of DC in the interface fraction was quantified following analysis on a flow cytometer (FACS). The cells were characterized to be negative for cell phenotype markers CD3 (T-cells), CD14 (monocytes), CD16 (NK cells) and CD20 (B-cells) and positive for HLA class II expression using dual staining with HLA-DR (on the FITC channel) and a cocktail of CD3, CD14, CD16, CD20 (on the PE channel). Dual staining with IgG2a on both the FITC and PE channels was used as isotype control. This phenotype is characteristic of DC (Macatonia, et al., 1991; Markowicz and Engleman, 1990; Young and Steinman, 1987).

A representative FACS profile obtained for the DC enriched cells obtained using methods of the present invention is shown in FIG. 1. The DC purity in this profile is approximately 16.0%. On average, 0.9±0.7×10$^6$ (meanjsd) DC with a purity of 15.4±10.1% (mean[]sd) were obtained from one unit of blood (n=60).

The morphology of the cells was also evaluated using photomicroscopy. These studies indicated that the DC enriched fraction contained large sized veiled cells with cytoplasmic processes extending from the cell surface, features characteristic of DC.

The methods described above were also applied in the isolation of a monocyte-depleted cell fraction containing DPC, where the fraction was cultured in a serum-free medium for a period sufficient to produce a morphological change in dendritic-precursor cells to cells having the characteristics (e.g., morphological characteristics) of dendritic cells. Four different serum-free media were tested: DMEM/F-12 (Gibco/BRL Life Technologies), Enriched Macrophage SFM (Gibco/BRL Life Technologies, AIM-V (Cat #12055, Gibco/BRL Life Technologies), and Enriched AIM-V (Gibco/BRL Life Technologies). The cells were then further purified using MEP as described above, and evaluated for purity and yield of DC cells, as described above. The results of these experiments are presented in Table 2, below.

TABLE 2

| Medium | n | Purity % | Yield % | # of DC/Buffy |
| --- | --- | --- | --- | --- |
| RPMI + 5% AB serum | 3 | 7.51 ± 0.84 | 0.21 ± 0.7 | 0.84 ± 0.28 × 10$^6$ |
| DMEM: F-12 (1:1) | 3 | 16.66 ± 5.15 | 0.28 ± 0.14 | 1.12 ± 0.56 × 10$^6$ |
| Enriched Macrophage SFM | 3 | 19.06 ± 2.59 | 0.40 ± 0.09 | 1.60 ± 0.36 × 10$^6$ |
| AIM-V | 2 | 15.50 ± 9.50 | 0.35 ± 0.28 | 1.40 ± 1.12 × 10$^6$ |
| Enriched AIM-V | 2 | 19.50 ± 4.50 | 0.38 ± 0.17 | 1.52 ± 0.68 × 10$^6$ |

The results demonstrate that the percent of DC present in fractions cultured in serum-free media (purity) is significantly greater than the purity in fractions cultured in the serum-containing control (RPMI+5% ABS). Results of additional experiments performed in support of the present invention indicated that the addition of 50 pg/mL GMCSF (Granulocyte Macrophage Colony Stimulating Factor) did not increase the purity or yield of DC.

EXAMPLE 2

Generation of Peptide-Specific Cytotoxic T-Lymphocytes

The isolated cells were further confirmed to be DC by demonstrating that they retained the ability to activate naive T-cells in vitro using HLA class I binding peptides. DC and T-lymphocyte fractions were obtained following density gradient separation of peripheral blood mononuclear cells. The DC enriched fraction was pulsed with the HLA-A*0201 binding HTLV-1 peptide (SEQ ID NO:l) and cultured with autologous T-lymphocytes to generate peptide-specific CTL.

The DC enriched fraction contained 8.6×10$^6$ cells and the lymphocyte enriched fraction contained 139.0× 10$^6$ cells. FACS analysis indicated DC purity of 8.0% in the DC-enriched fraction, resulting in 0.69×10$^6$ DC. In this instance, 2.0×10$^6$ interface cells (160,000 DC) were incubated with 1.0 μg/mL β2-microglobulin and 5.0 μg/mL HTLV-1 peptide (SEQ ID NO:1) for 2 hours at 37° C. The remaining DC were used to generate CTL using other HLA-A*0201 binding peptides.

Figure 10:
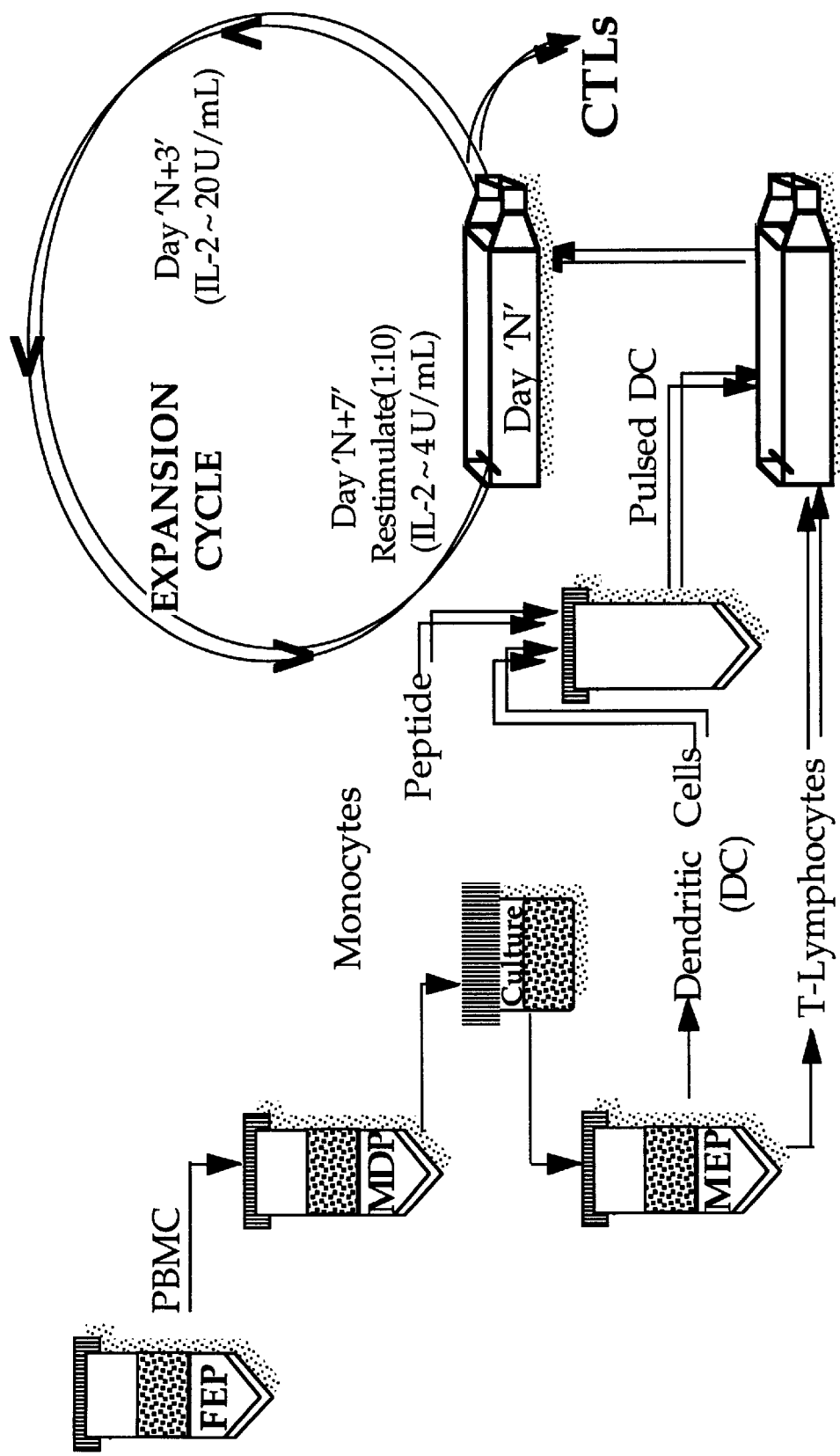
FIG. 10 shows a schematic of one embodiment of CTL expansion in response to activation by PAP cells isolated using methods of the present invention.

The lymphocyte fraction had the following phenotype distribution when stained and analyzed on the FACS: 70.8% CD3$^+$, 49.3% CD4$^+$ and 22.8% CD8$^+$. This fraction (14.0× 10$^6$ cells; 3.2×10$^6$ CD8$^+$ cells) was mixed with the HTLV-1 peptide pulsed DC-enriched cells, resulting in a DC to CD8$^+$ T-lymphocyte ratio of 1:20. Cultures were initiated at an inoculum concentration of 0.8×10$^6$ cells/mL in AB Culture Medium supplemented with 4.0 U/mL of IL-2. CTL were expanded by restimulating every 7 days with HTLV-1 peptide pulsed autologous monocytes and IL-2 cycling as described in the Materials and Methods for a total of 41 days, resulting in 145.0×10$^6$ cells containing 70.7% CD8$^+$ T-cells. A schematic summary of this expansion protocol is shown in FIG. 10.

Figure 2A:
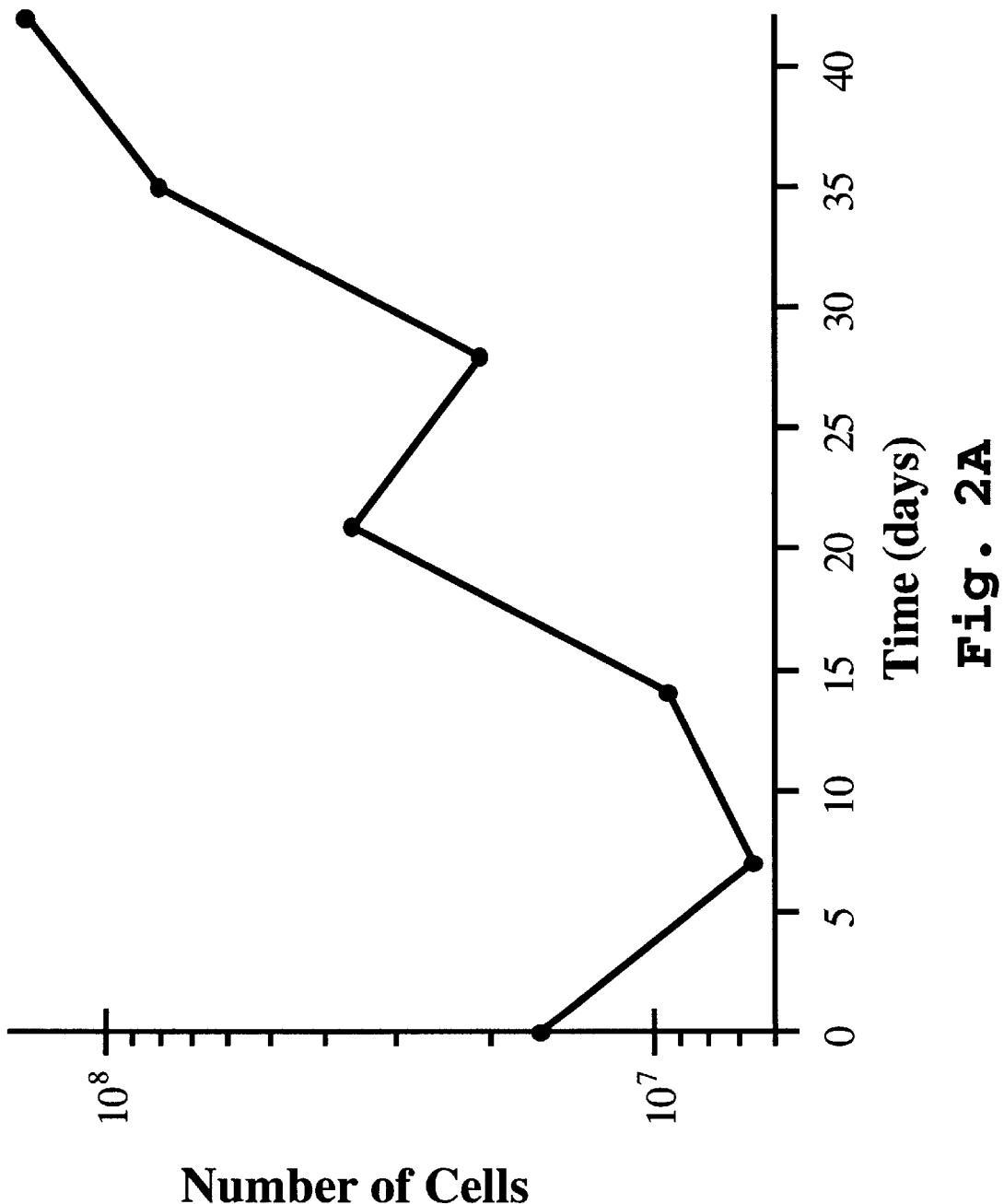
FIGS. 2A and 2B show the growth kinetics of T-lymphocytes (T-cells) stimulated with autologous DC that had been pulsed with HTLV-1 tax 11–19 peptide (SEQ ID NO:1). The T-cells were subsequently restimulated weekly with HTLV-1 peptide-pulsed autologous monocytes to generate HTLV-1 peptide specific $CD8^+$ cytotoxic T-lymphocytes (CTL). An inoculum of $14.0 \times 10^6$ cells containing 22.8% $CD8^+$ T-cells was expanded to $145.0 \times 10^6$ cells containing 70.7% $CD8^+$ T-cells following 41 days of culture (FIG. 2A). The growth kinetics from a similar experiment are shown in FIG. 2B.

FIG. 2A shows the growth kinetics of the CTL stimulated with the HTLV-1 peptide-pulsed autologous dendritic cells. Cell number initially decreases, possibly due to death of bystander cells, for approximately the first 10–12 days of culture. At day 14, during the second restimulation, the number of cells was nearly the same as the inoculated number of cells, presumably with a higher frequency of peptide-specific T-lymphocytes. Thereafter the CTL, selected by manner of antigen-specific restimulation, can be expanded beyond 40 days of culture. The specific growth rate of peptide-specific CTL from day 14 to day 41 was calculated to be 0.006 hr$^{-1}$, resulting in a doubling time of 4.9 days and a 45-fold expansion based on the number of inoculated CD8$^+$ cells.

Figure 2B:
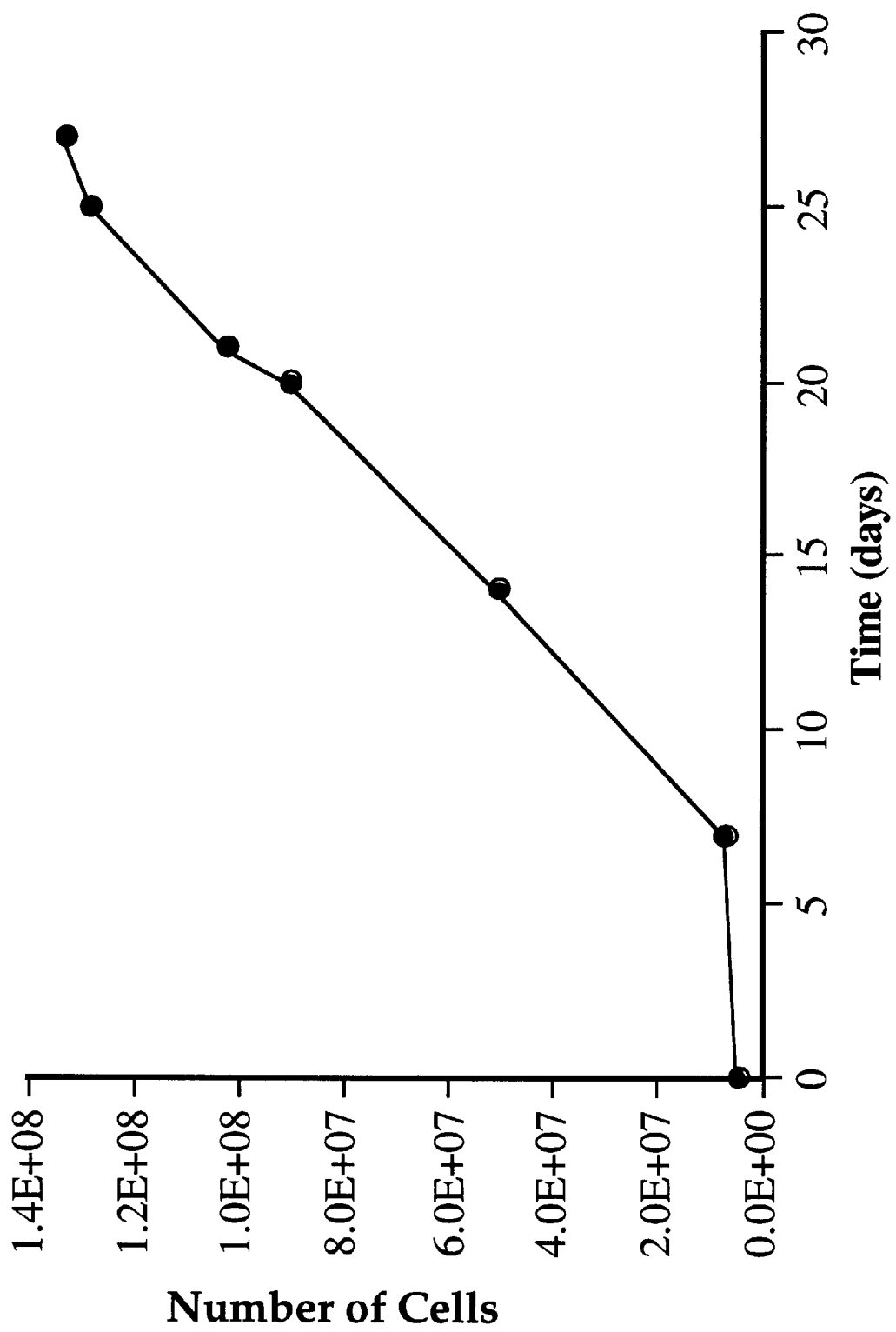

FIG. 2B shows the results of a similar experiment, showing the kinetics of expansion of CTL line R54, generated from 250 ml peripheral blood of a HTLV-1 seronegative individual using the HTLV-1 tax 11–19 peptide (SEQ ID NO:1). The cells expanded to over $120\times10^6$ cells after three weeks of culture, and were comprised predominantly of $CD4^+$ and $CD8^+$ T lymphocytes.

EXAMPLE 3

Figure 3A:
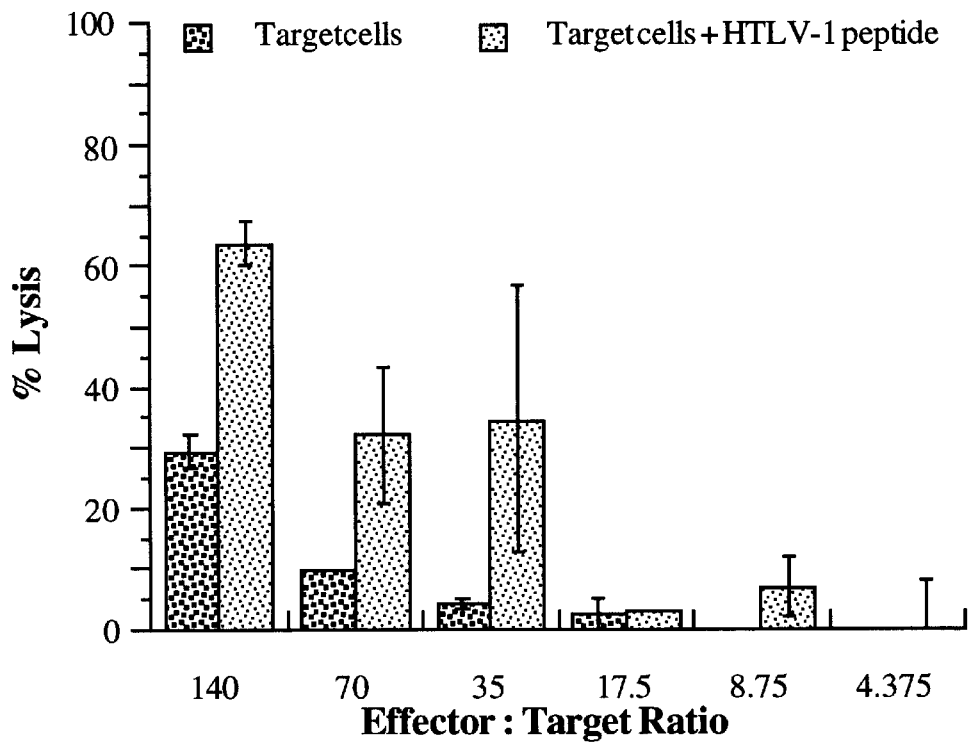
FIGS. 3A and 3B show antigen-specific lysis, measured in standard 4 hour $^{51}Cr$ release assay, of target (JY) cells that had been pulsed with the HTLV-1 peptide, as well as unpulsed control JY cells, by cultured T-lymphocytes that had been activated by exposure to HTLV-1 peptide-pulsed DC.
Figure 3B:
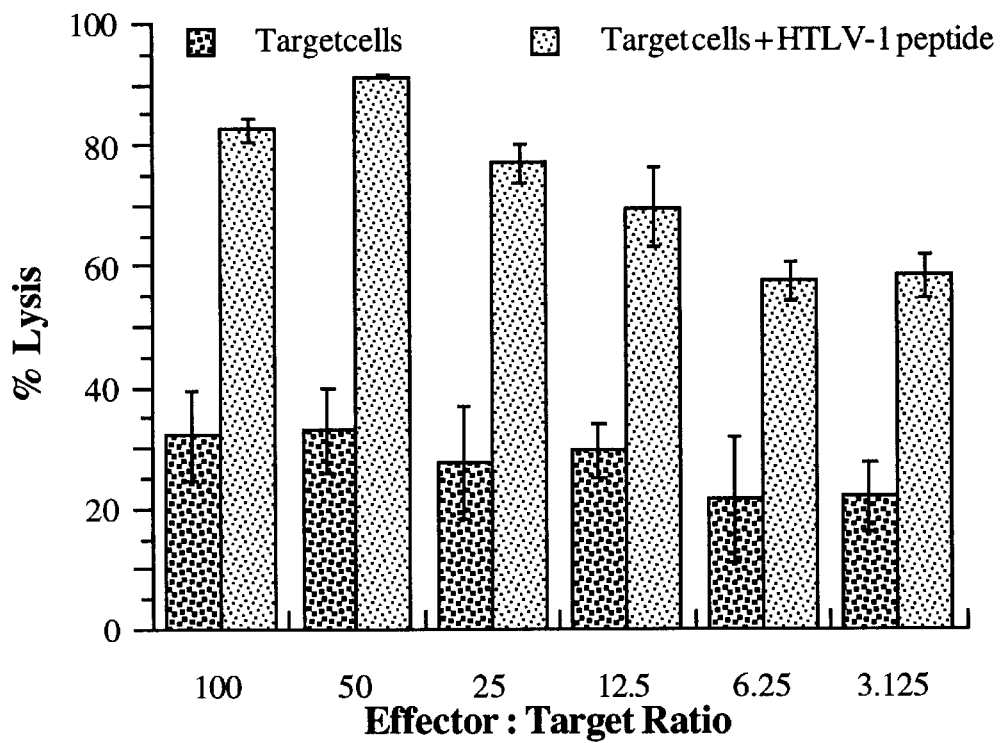

Lysis of HTLV-1 Peptide-Pulsed JY Cells by Activated Aytotoxic T-Lymphocytes CTL from the culture described in Example 2 were tested on day 34 and day 41 for their ability to lyse HTLV-1 peptide-pulsed JY target cells in a standard 4 hour $^{51}Cr$ release cytotoxicity assay (Materials and Methods). The results, shown in FIGS. 3A and 3B, indicated a dose response curve dependent antigen-specific lysis of peptide pulsed target cells. On day 34 (FIG. 3A), at the highest effector:target ratio of 142:1, measured lysis of HTLV-1 peptide-pulsed JY cells was calculated to be 63.5±3.5% (mean±sd) with a background lysis with unpulsed JY cells of 29.1±2.9% (mean±sd). On day 41 (FIG. 3B), at the highest effector:target ratio of 100:1 (lower than that on day 34), 82.3±1.9% (mean±sd) and 31.8±7.5% (mean±sd) lysis was observed for HTLV-1 peptide pulsed and unpulsed JY target cells, respectively. These results indicate that the antigen-specific cytotoxicity exhibited by generated CTL is maintained over a 40 day expansion period.

As illustrated in FIGS. 3C and 3D, the observed antigen-specific lysis of peptide-pulsed target cells (JY cells in FIG. 3C and T2 cells in FIG. 3D) was inhibited to levels similar to that obtained with unpulsed target cells in the presence of W6/32, a monoclonal antibody directed against HLA class I molecules. Additionally, antigen-specific cell lysis was observed to be inhibited by the addition of OKT-8 (an antibody directed against the CD8 molecules on the T-lymphocyte surface), whereas an anti-HLA class II antibody had no effect on antigen specific lysis. These results indicate that the antigen-specific lysis is primarily HLA class I restricted and CD8+T-lymphocyte mediated.

The experiments described above were performed with HTLV-1 tax 11–19 peptide-specific CTL lines generated from the peripheral blood of 13 HLA-A2 positive, HTLV-1 seronegative individuals. Antigen-specific CTL were generated from 11 of the 13 samples.

CTL generated against HTLV-1 peptide using peptide-pulsed DC were tested for their ability to lyse target cells endogenously expressing the HTLV-1 antigens. The target cells were derived from two cell lines—MJ cells, a T-cell line obtained from the ATCC, and 20473 cells, a B-cell line obtained from Merck Sharp and Dohme Research Laboratories (Rahway, N.J.). MJ cells are HLA-A*0201 negative (A2.1⁻) T cells which have been infected with HTLV-1 and which synthesize HTLV-1 antigens in culture (A2.1⁻ tax⁺ T cells). A sample of MJ cells was transfected with HLA-A*0201 using transient vaccinia vector, rendering the transfected cells HLA-A*0201 positive (A2.1⁺ tax⁺ T cells). 20473 cells are an HLA-A*0201 positive transfected B-cell line obtained by insertion of a plasmid containing the Tax protein of the HTLV-1 along with a hygromycin selection gene (A2.1⁺ tax⁺ B cells). JY cells were used as the A2.1⁺ tax⁻ B-cell controls.

Figure 4:
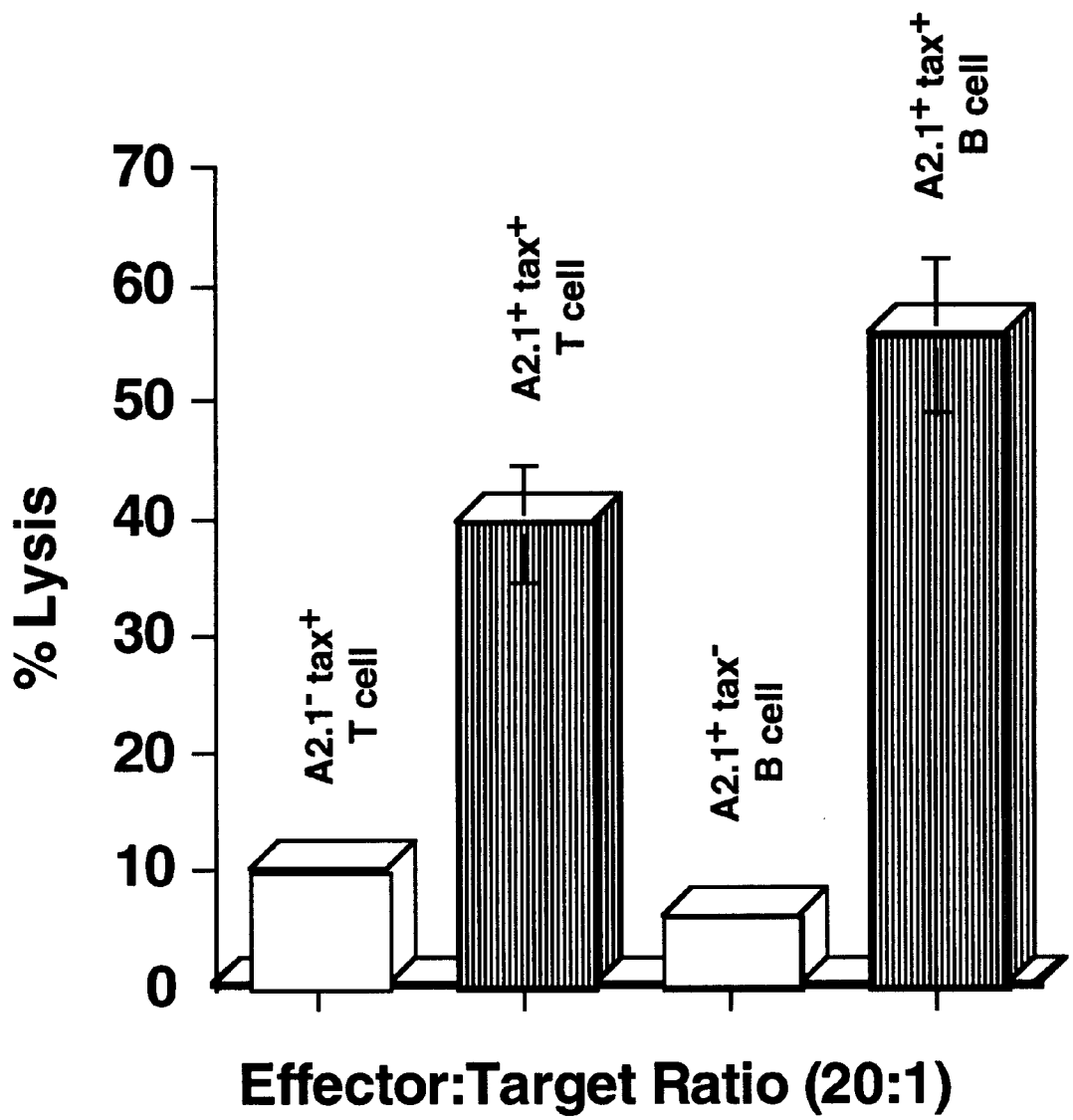
FIG. 4 shows lysis of target cells endogeneously expressing HTLV-1 antigens by CTL activated against HTLV-1 peptide with HTLV-1 peptide-pulsed DC.

As is illustrated in FIG. 4, HTLV-1 specific CTL recognized and lysed both the HLA-A*0201-transfected MJ cells and the 20473 cells. At an effector to target ratio of 20:1 the lysis of untransfected M cells and transfected MJ cells was 9.72% and 39.43% respectively; and that for 20473 cells was 55.74% over a background of 6.64% with JY cells. Thus, the HTLV-1 peptide is recognized in an antigen specific, HLA-A*0201 restricted manner. These data demonstrate that the generated CTL lyse not only peptide pulsed/coated target cells, but also cells which are endogeneously expressing the antigen or have been virally-infected (more analogous to an in vivo situation than peptide-pulsed cells).

EXAMPLE 4

Phenotype Analysis of Activated T-Lymphocytes

Figure 5:
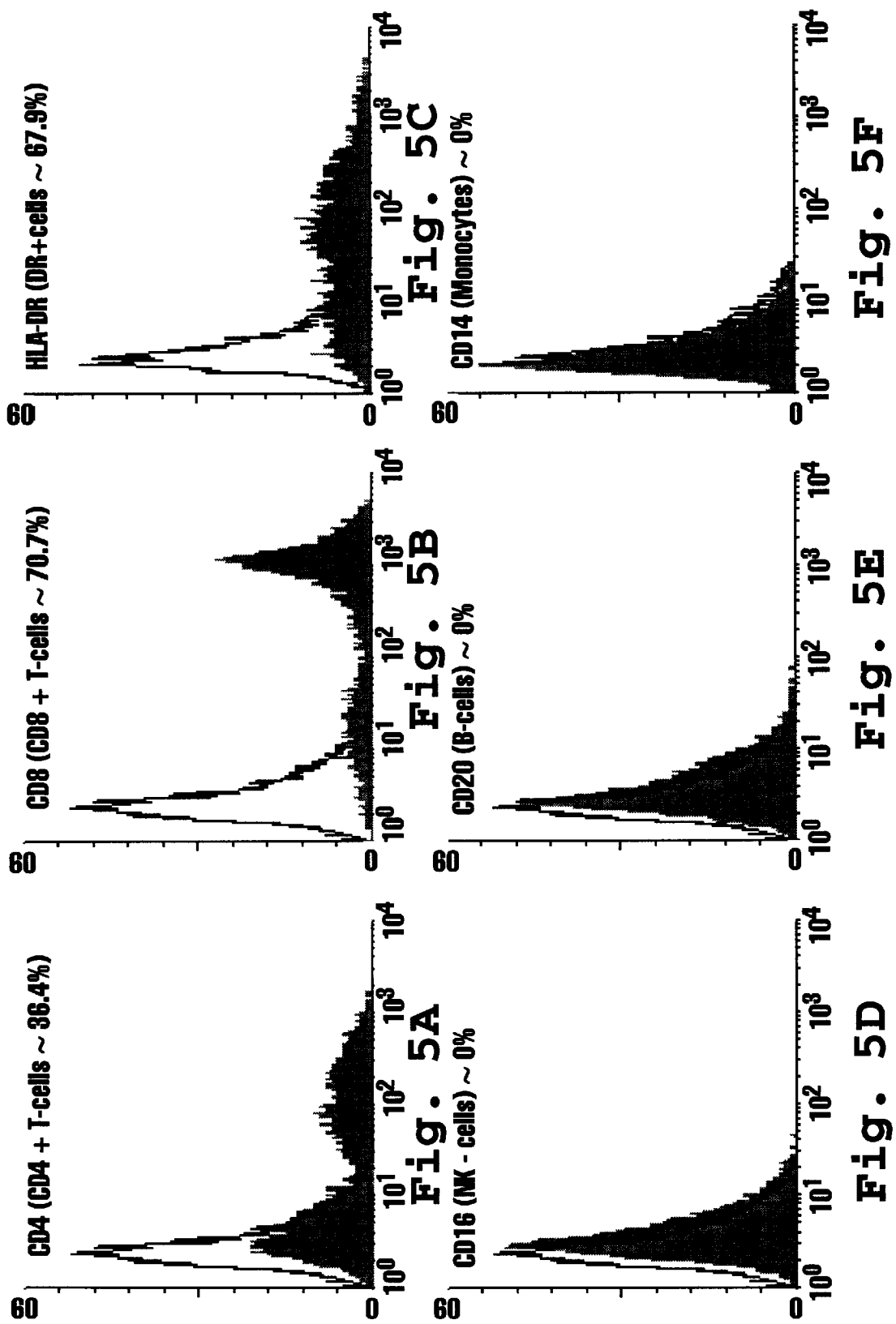
FIGS. 5A to 5F show the FACS profiles (filled histograms) for T-lymphocytes on day 41 of culture obtained using the indicated markers. A line histogram for the isotype control for each cell surface marker is shown superimposed on the FACS profiles.

Cell phenotype analysis of the CTL described in Examples 2 and 3 was performed using FACS on day 34 and day 41 of culture. The results, shown in FIG. 5, indicate that the majority of cells were either $CD4^+$ or $CD8^+$ T-lymphocytes, with no detectable numbers of NK, B or monocytic cells. Populations corresponding to cells surface markers for monocytes (CD14), NK cells (CD16) or B-cells (CD20) were not detected. Additionally, 67.9% of the cells also expressed the activation marker HLA-DR, indicating that a significant fraction of the T-lymphocytes were activated and presumably proliferating. A line histogram for the isotype control for each cell surface marker is shown superimposed on the FACS profiles (filled histograms).

Figure 6:
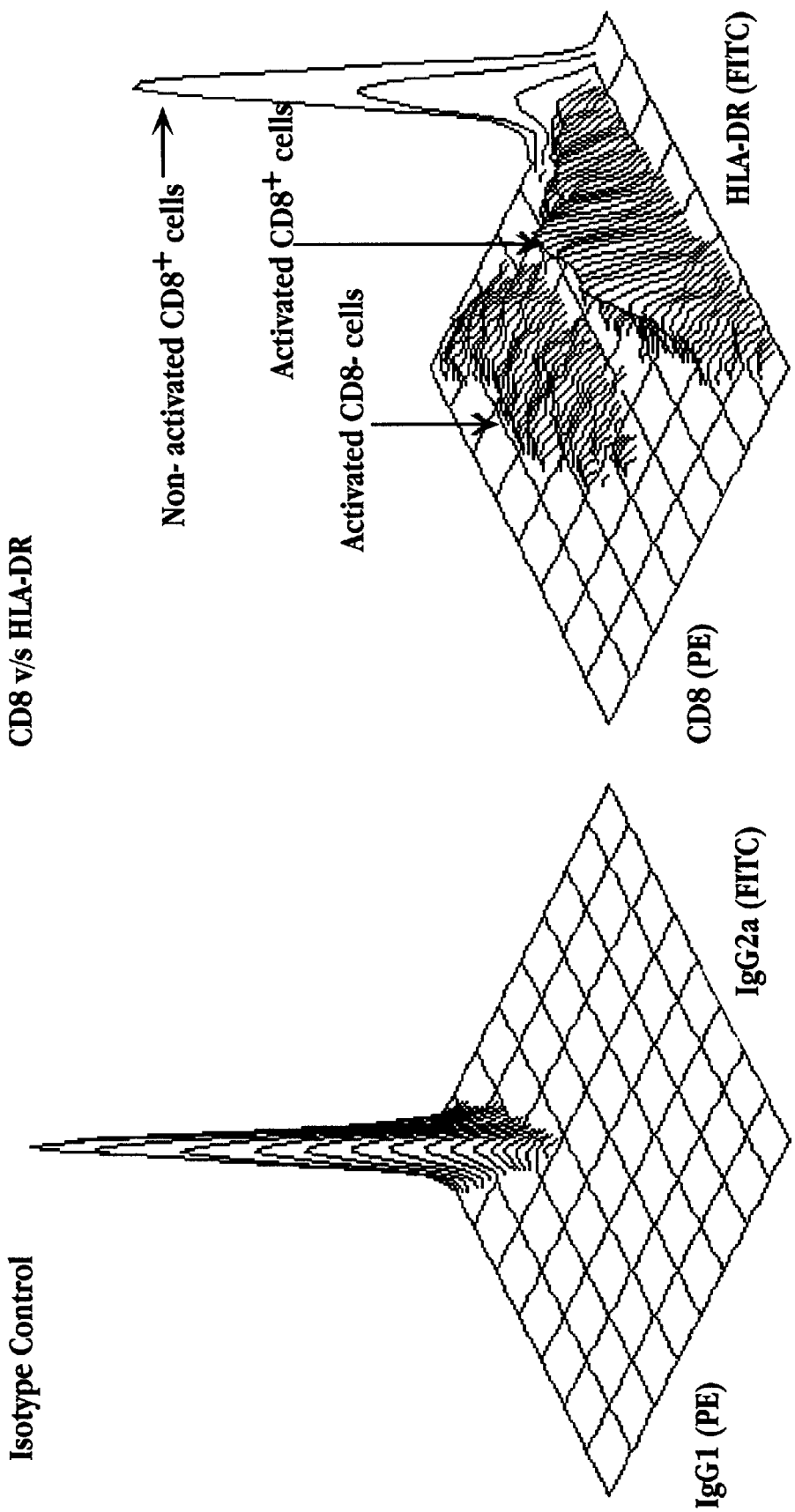
FIGS. 6A and 6B show FACS profiles of dual staining with CD8 and HLA-DR antibodies, illustrating that most of the CD8+ T-lymphocytes express the activation marker HLA-DR (FIG. 6B). IgG1 (PE channel) and IgG2a (FITC channel) were used as the isotype controls (FIG. 6A).

Dual staining with HLA-DR and CD8 on day 41, shown in FIGS. 6A and 6B, indicated that 62.2% of the cells were both HLA-DR⁺ and CD8⁺, 13.8% cells were HLA-DR⁻ but CD8⁺ and 4.6% cells were HLA-DR⁺ and CD8⁻. This indicates that the majority of cells which were activated, as judged by HLA-DR expression, expressed the CD8 molecule on the cell surface, confirming that the expansion protocol led to selective expansion of antigen-specific activated CD8⁺ T-lymphocytes.

The relative proportion of CD4⁺, CD8⁺ and HLA-DR⁺ cells in culture is summarized in Table 3, below.

TABLE 3

| Day | % CD4 | % CD8 | % HLA-DR |
| --- | --- | --- | --- |
| 02 | 49.3 | 22.8 | N.D. |
| 34 | 43.7 | 58.4 | 60.7 |
| 41 | 36.4 | 70.7 | 67.9 |

The cell phenotype distributions were obtained following FACS staining of T-lymphocyte cultures following initiation of culture (day 2), intermediate time point (day 34) and end of culture (day 41). The results indicate an increase in the fraction of CD8⁺ T-lymphocytes and a decrease in CD4⁺ T-lymphocyte fraction with prolonged culture. On both day 34 and day 41, the culture is predominantly constituted of CD4⁺ and CD8⁺ T-lymphocytes. A majority of CD8⁺ T-lymphocytes at the end of culture expressed the activation marker HLA-DR. These date indicate the ability to selectively expand CD8⁺ T-cells in these cultures to generate CTL with potent peptide-specific lytic capability.

EXAMPLE 5

Lysis of HIV R Pol 464–472 Peptide-Pulsed JY Cells by Activated Cytotoxic T-Lymphocytes PAP cells pulsed with the HIV RT Pol 464–472 peptide (SEQ ID NO:3) as described in the Materials and Methods were used to activate CD8⁺ T-lymphocytes (CTL) at a ratio of 1:10. Cultures were initiated at an inoculum concentration of $0.5\times10^6$ cells/mL in AB Culture Medium supplemented with 4.0 U/mL of IL-2. CTL were expanded by restimulating every 7 days with HIV Pol 464–472 peptide-pulsed autologous monocytes and IL-2 cycling as described above for a total of 21 days, resulting in $12.8\times10^6$ cells.

Figure 7:
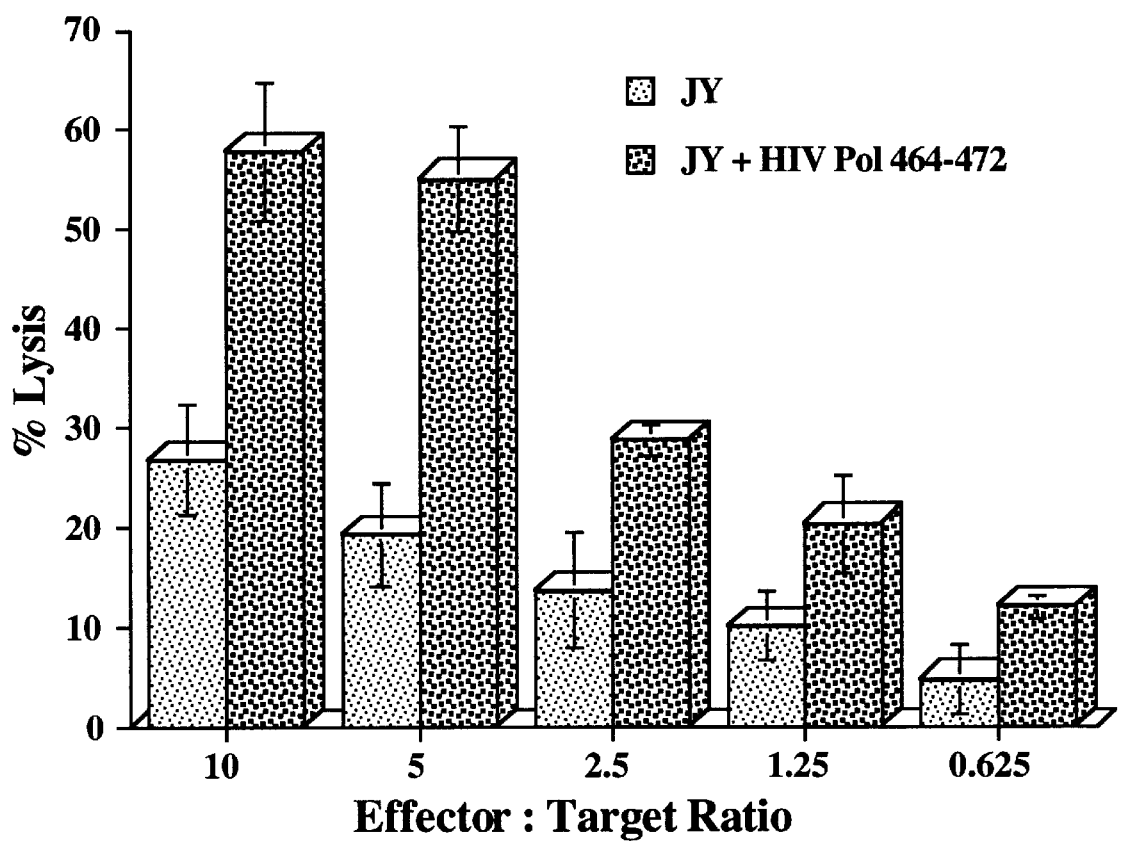
FIG. 7 shows antigen-specific lysis, measured in standard 4 hour $^{51}Cr$ release assay, of target (JY) cells that had been pulsed with the HIV RT Pol 464–472 peptide (SEQ ID NO:3), as well as unpulsed control JY cells, by cultured T-lymphocytes that had been activated by exposure to HIV peptide-pulsed DC.

CTL described above were tested on day 28 for their ability to lyse HIV Pol 464–472 peptide-pulsed JY target cells in a 4 hour $^{51}$Cr release cytotoxicity assay (Materials and Methods). The results, shown in FIG. 7, indicated a dose response curve dependent antigen-specific lysis of peptide pulsed target cells. At the highest effector:target ratio of 10:1, measured lysis of HIV Pol 464–472 peptide-pulsed JY cells was calculated to be 57.9±6.9% (meanjsd) with a background lysis with unpulsed JY cells of 26.9±5.6% (meanjsd). These results support the conclusions reached in Example 3, above, and demonstrate that antigen-specific cytotoxicity can be generated against different peptides.

EXAMPLE 6

Lysis of MART-1 Peptide-Pulsed JY Cells by Activated Cytotoxic T-Lymphocytes

PAP cells were pulsed with the MART-1 peptide (SEQ ID NO:2) and used to activate and expand CTL as described above. The activated CTL were evaluated for their ability to lyse MART-1 peptide-pulsed JY target cells, unpulsed JY cells, K562 cells, Malme-3 cells (A2 negative melanoma cell line that expresses MART-1 antigen), SK-MEL-28 cells (A2 positive line that does not express MART-1 antigen) and SK-MEL-5 cells (A2 positive line that expresses MART-1 antigen).

The results show that CTL activated by MART-1 peptide-pulsed PAP were effective to lyse MART-1 peptide-pulsed JY cells, as well as the positive control SK-MEL-5 cells, at levels significantly higher than the negative control cells. Further, the results demonstrate that the CTL can lyse cells that endogenously express the MART-1 antigen.

EXAMPLE 7

Three-Dimensional Culture of Dendritic Cells

Pulsed or stimulated dendritic cells were maintained in a 3-dimensional cross-linked collagen matrix for up to 12 days with no loss of ability to activate CTL. The collagen matrix was prepared by mixing three volumes of "VITROGEN-100" (2.9 mg/mL Type 1 collagen in 0.012 N HCl solution; Collagen Corp., Palo ALto, Calif.) with one volume of four-fold concentrated AB culture medium at 4° C., pH 7.2 (adjusted with 1.0 N NaOH).

Dendritic cells in culture were pelleted by a brief spin and were dispersed in the collagen suspension. The resulting cell-collagen mixture was then poured into multiwell plates to a final gel thickness of approximately 1 mm.

The cell/collagen mixtures were transferred to an incubator at 37° C. to initiate gelation of the collagen. Gelation typically occurred in 15–20 minutes, entrapping the cells within a highly porous three dimensional network of collagen fibers. After gelation was complete, medium was added on top of the gelled plug in each well and the cultures were incubated at 37° C. in a 5% $CO_2$ incubator.

In one series of experiments, DC entrapped in collagen gel were pulsed with HTLV-1 peptide and used to stimulate autologous T-lymphocytes essentially as described above. The reagents (including the "pulsing" peptide and the T-cells) were added to the medium bathing the collagen plug containing the DC. After 21 days of culture (with weekly restimulation with autologous peptide pulsed monocytes and IL-2 feeding schedule as described above), activated CTL were released from the collagen gel by digestion with collagenase.

Figure 8:
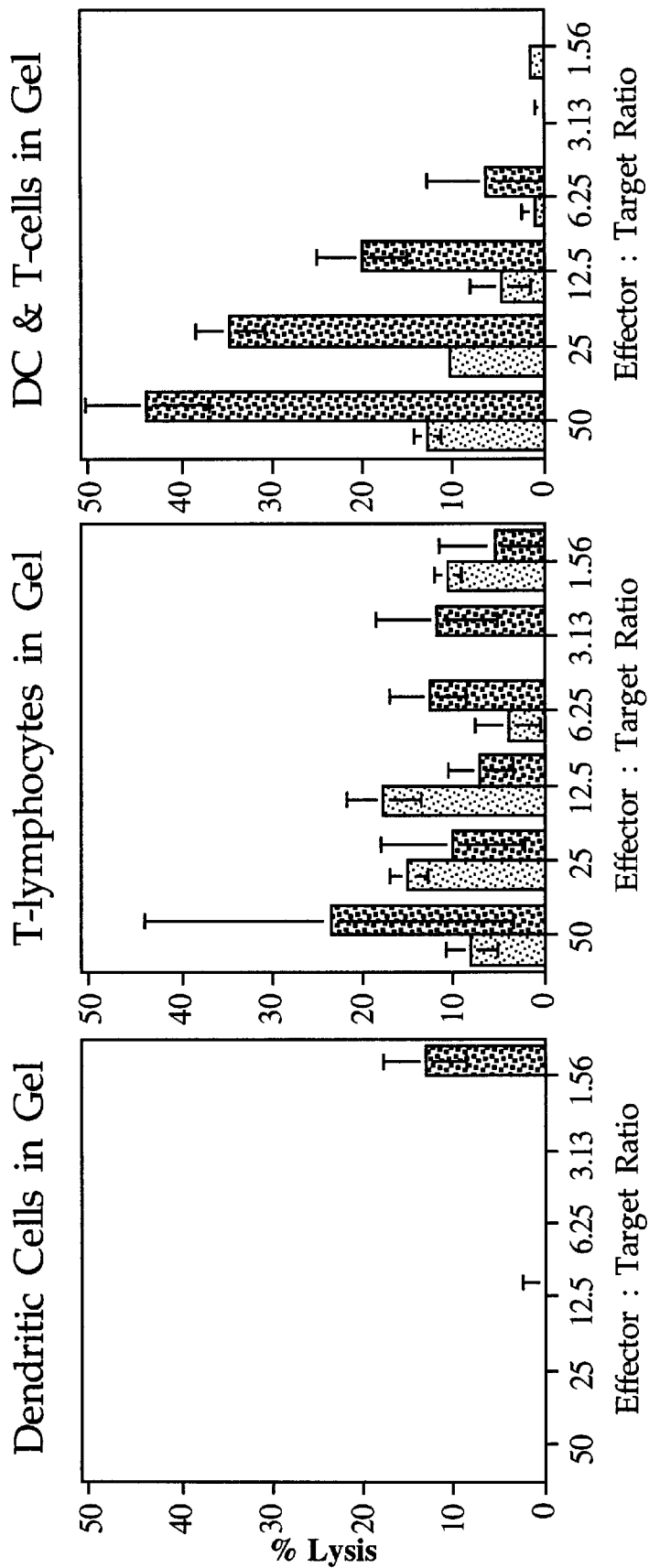
FIGS. 8A, 8B and 8C show antigen-specific lysis, measured in standard 4 hour $^{51}Cr$ release assay, of target (JY) cells that had been pulsed with the HIV RT Pol 464–472 peptide (SEQ ID NO:3), as well as unpulsed control JY cells, by cultured T-lymphocytes that had been activated by exposure to HTLV-1 tax peptide-pulsed DC embedded in a collagen gel.

The released cells were used in standard cytotoxicity assays as described above. Collagen entrapment culture of T-lymphocytes alone (FIG. 8B) or DC alone (FIG. 8A) were used as controls. CTL generated by HTLV-1 pulsed entrapped DC exhibited potent peptide specific lysis of HTLV-1 peptide pulsed target cells (JY) with low background lysis of unpulsed JY cells (FIG. 8C). The control cultures (FIGS. 8A and 8B) demonstrated no appreciable antigen-specific lysis over detectable background killing.

While the invention has been described with reference to specific methods and embodiments, it will be appreciated that various modifications and changes may be made without departing from the invention.

What is claimed is:

1. A cell composition comprising potent antigen presenting (PAP) cells, prepared by obtaining from a human blood sample, a monocyte-depleted cell fraction containing peripheral blood lymphocytes and dendritic-precursor cells, culturing the cell fraction in a serum-free medium for a period sufficient to produce a morphological change in dendritic-precursor cells to cells having the characteristics of dendritic cells, harvesting non-adherent cells produced by said culturing, enriching the portion of dendritic cells in the harvested cells by density centrifugation, to obtain a fraction enriched in PAP cells, and entrapping said PAP-enriched fraction in a three-dimensional matrix;

said cell composition characterized by (i) a phenotype that is positive for surface antigen HLA DR and negative for surface antigens CD3, CD14, CD16, and CD20, (ii) the ability to elicit primary and secondary immune responses when co-cultured with human lymphocytes in culture, entrapped in a three-dimensional matrix, (iii) serum-free conditions, and (iv) a lack of exocenously supplied cytokines.

2. The composition of claim 1, wherein the three-dimensional matrix is a cross-linked collagen matrix.

3. The composition of claim 1, wherein the entrapped cells include at least 10% dendritic cells.

4. The composition of claim 1, wherein the entrapped cells include at least 50% dendritic cells.

5. The composition of claim 1, wherein the PAP cells in said matrix are modified in a manner effective to result in presentation of a selected antigen in association with class I major histocompatibility complex (MHC-I).

6. The composition of claim 5, wherein the selected antigen is a tumor or viral antigen.

7. The composition of claim 1, wherein said enriching step is carried out by layering said cells over a separation medium selected from the group consisting of a separation medium having a density of 1.0650±0.0010 g/mL and an osmolarity of 300±15 mosm, a separation medium having a density of 1.0800±0.0010 g/mL and an osmolarity of 540±25 mOsm, and a separation medium having a density of 1.0550±0.0010 g/mL and an osmolarity of 290±15 mOsm.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 9 amino acids
      (B) TYPE: amino acid
      (C) STRANDEDNESS: single
      (D) TOPOLOGY: unknown (ii) MOLECULE TYPE: peptide (iii) HYPOTHETICAL: NO (iv) ANTI-SENSE: NO (vi) ORIGINAL SOURCE:
      (C) INDIVIDUAL ISOLATE: Peptide HTLV-1 Tax 11-19 Pep (xi) SEQUENCE DESCRIPTION: SEQ ID NO:1:

Leu Leu Phe Gly Tyr Pro Val Tyr Val
1            5

```
(2) INFORMATION FOR SEQ ID NO:2:

(i) SEQUENCE CHARACTERISTICS:
         (A) LENGTH: 9 amino acids
         (B) TYPE: amino acid
         (C) STRANDEDNESS: single
         (D) TOPOLOGY: unknown (ii) MOLECULE TYPE: peptide (iii) HYPOTHETICAL: NO (iv) ANTI-SENSE: NO (vi) ORIGINAL SOURCE:
         (C) INDIVIDUAL ISOLATE: Peptide MART-1 Pep (xi) SEQUENCE DESCRIPTION: SEQ ID NO:2:

Ala Ala Gly Ile Gly Ile Lys Thr Val
1               5

(2) INFORMATION FOR SEQ ID NO:3:

(i) SEQUENCE CHARACTERISTICS:
         (A) LENGTH: 9 amino acids
         (B) TYPE: amino acid
         (C) STRANDEDNESS: single
         (D) TOPOLOGY: unknown (ii) MOLECULE TYPE: peptide (iii) HYPOTHETICAL: NO (iv) ANTI-SENSE: NO (vi) ORIGINAL SOURCE:
         (C) INDIVIDUAL ISOLATE: Peptide HIV Pol 464-472 Pep (xi) SEQUENCE DESCRIPTION: SEQ ID NO:3:

Ile Leu Lys Glu Pro Val His Gly Val
1               5
```